United States Patent
Hayashi et al.

(10) Patent No.: US 7,129,715 B2
(45) Date of Patent: Oct. 31, 2006

(54) OIL DETERIORATION SENSOR

(75) Inventors: Shinichi Hayashi, Mizunami (JP); Hisashi Sasaki, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/491,124

(22) PCT Filed: Sep. 30, 2002

(86) PCT No.: PCT/JP02/10158

§ 371 (c)(1),
(2), (4) Date: Mar. 29, 2004

(87) PCT Pub. No.: WO03/029802

PCT Pub. Date: Apr. 10, 2003

(65) Prior Publication Data

US 2004/0263187 A1    Dec. 30, 2004

(30) Foreign Application Priority Data

Sep. 28, 2001   (JP)   ............................. 2001-303557

(51) Int. Cl.
*G01R 27/26*   (2006.01)

(52) U.S. Cl. ...................... 324/685; 324/658; 324/686; 73/53.05

(58) Field of Classification Search ................ 324/553, 324/698, 658–665, 686–690, 685; 73/53.05, 73/53.06, 53.07, 54.01, 54.02
See application file for complete search history.

(56) References Cited

U.S. PATENT DOCUMENTS

| | | | |
|---|---|---|---|
| 4,733,556 A | 3/1988 | Meitzler et al. | |
| 4,775,830 A | 10/1988 | Lyyra | |
| 4,831,325 A * | 5/1989 | Watson, Jr. | 324/678 |
| 5,540,086 A * | 7/1996 | Park et al. | 73/53.05 |
| 5,592,098 A * | 1/1997 | Suzuki et al. | 324/663 |
| 5,789,665 A * | 8/1998 | Voelker et al. | 73/53.05 |
| 5,929,754 A * | 7/1999 | Park et al. | 340/439 |
| 6,028,433 A | 2/2000 | Cheiky-Zelina et al. | |
| 6,250,152 B1 | 6/2001 | Klein et al. | |
| 6,268,737 B1 | 7/2001 | Marszalek | |
| 6,459,995 B1 * | 10/2002 | Collister | 702/23 |
| 6,463,796 B1 * | 10/2002 | Van Mullekom et al. | 73/118.1 |
| 6,490,920 B1 * | 12/2002 | Netzer | 73/304 C |
| 6,563,328 B1 * | 5/2003 | Lenormand et al. | 324/663 |

FOREIGN PATENT DOCUMENTS

EP    0 166706    1/1986

(Continued)

*Primary Examiner*—Anjan Deb
*Assistant Examiner*—Marina Kramskaya
(74) *Attorney, Agent, or Firm*—Sughrue Mion, PLLC

(57) ABSTRACT

An engine oil deterioration detection apparatus includes a sensing capacitor CS formed of paired electrodes dipped into engine oil whose deterioration is to be detected, the engine oil deterioration detection apparatus detecting deterioration of the engine oil on the basis of a change in electrostatic capacitance of the sensing capacitor CS. A measurement signal generation circuit generates a measurement signal to be supplied to the sensing capacitor CS. A detection signal output circuit outputs a detection signal on the basis of a response wave signal produced from the sensing capacitor CS in response to supply of the measurement signal thereto, the detection signal reflecting the electrostatic capacitance of the sensing capacitor CS. A temperature compensation mechanism is provided to compensate for a level change of the detection signal stemming from a temperature characteristic and/or a time-course deterioration of the detection signal output circuit.

15 Claims, 19 Drawing Sheets

FOREIGN PATENT DOCUMENTS

| | | | |
|---|---|---|---|
| GB | 2306660 A * | 5/1997 |
| JP | 59-102151 A | 6/1984 |
| JP | 60-262066 A | 12/1985 |
| JP | 62-018981 | 1/1987 |
| JP | 63-168549 A | 7/1988 |
| JP | 1-117544 U | 8/1989 |
| JP | 2-232516 A | 9/1990 |
| JP | 4-102069 A | 4/1992 |
| JP | 5-264324 | 10/1993 |
| JP | 5-264495 A | 10/1993 |
| JP | 11-507434 A | 6/1999 |
| JP | 11-295258 A | 10/1999 |

* cited by examiner

FIG. 3A
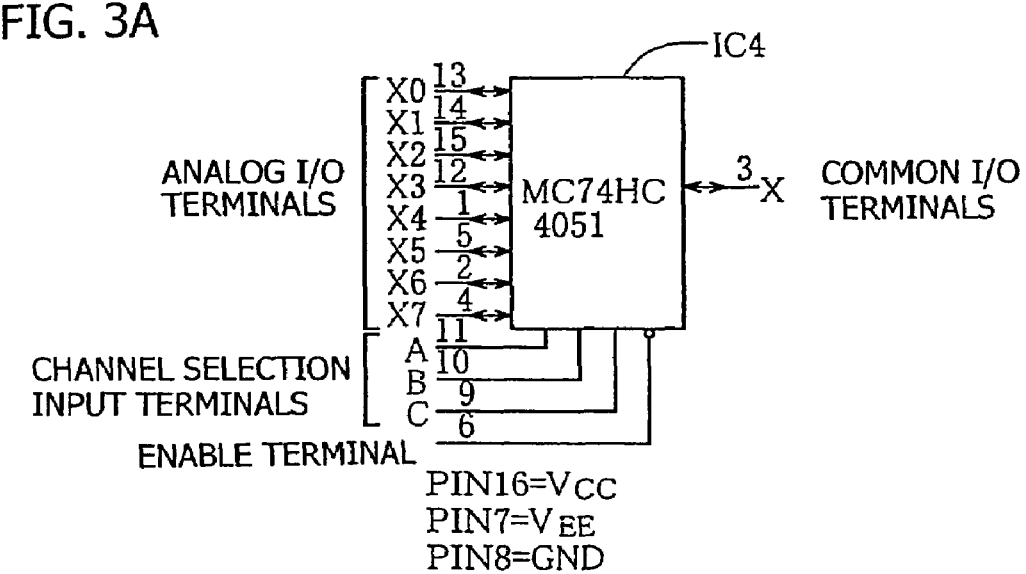
FIG. 3B
| CONTROL INPUT | | | | CHANNEL SELECTION INPUT |
|---|---|---|---|---|
| ENABLE TERMINAL | C | B | A | TURNED-ON CHANNEL |
| L | L | L | L | X0 |
| L | L | L | H | X1 |
| L | L | H | L | X2 |
| L | L | H | H | X3 |
| L | H | L | L | X4 |
| L | H | L | H | X5 |
| L | H | H | L | X6 |
| L | H | H | H | X7 |
| H | X | X | X | NO |
X = ARBITRARY
FIG. 3C
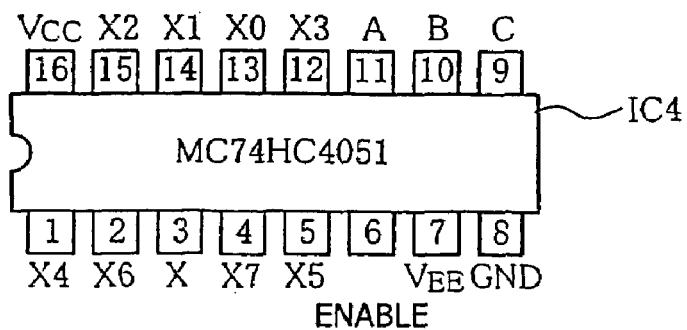

FIG. 7A
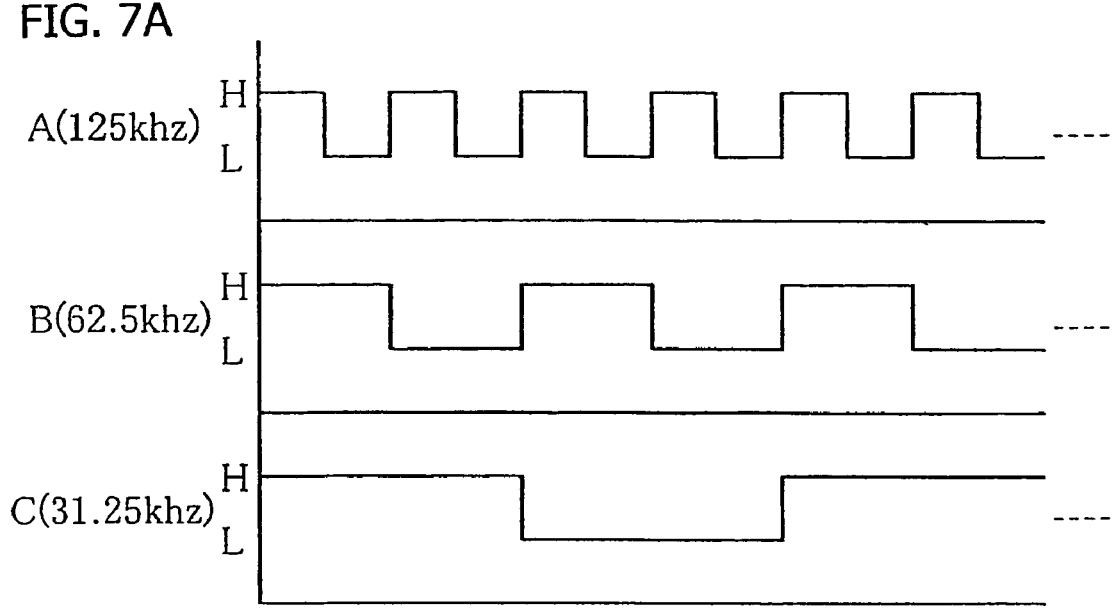
FIG. 7B
| A | H | L | H | L | H | L | H | L | H | L | H | L | ---- |
|---|---|---|---|---|---|---|---|---|---|---|---|---|------|
| B | H | H | L | L | H | H | L | L | H | H | L | L | ---- |
| C | H | H | H | H | L | L | L | L | H | H | H | H | ---- |
| ON-CHANNEL | X7 | X6 | X5 | X4 | X3 | X2 | X1 | X0 | X7 | X6 | X5 | X4 | ---- |
| VOLTAGE | $\delta$ | $\gamma$ | $\beta$ | $\alpha$ | $\beta$ | $\gamma$ | $\delta$ | $\varepsilon$ | $\delta$ | $\gamma$ | $\beta$ | $\alpha$ | ---- |
FIG. 7C
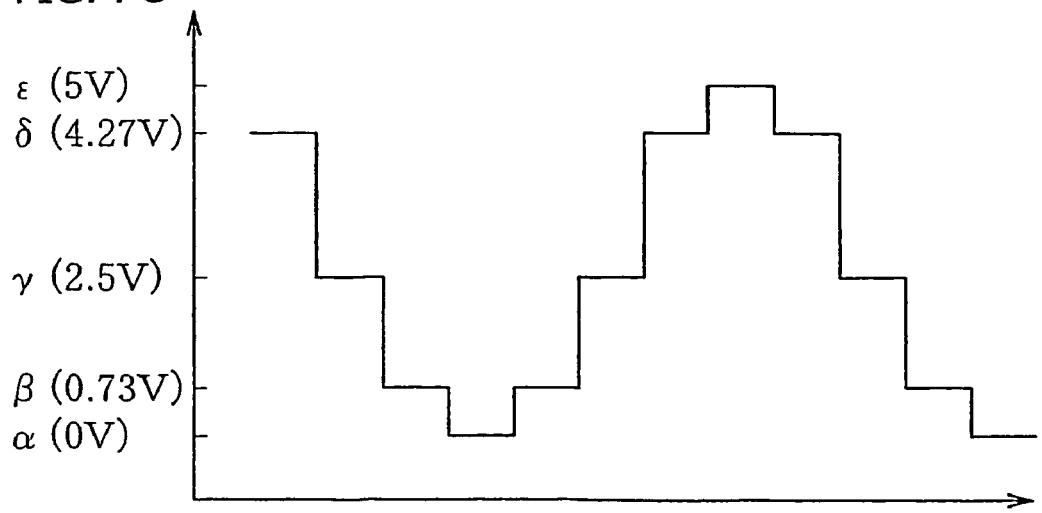

FIG. 8
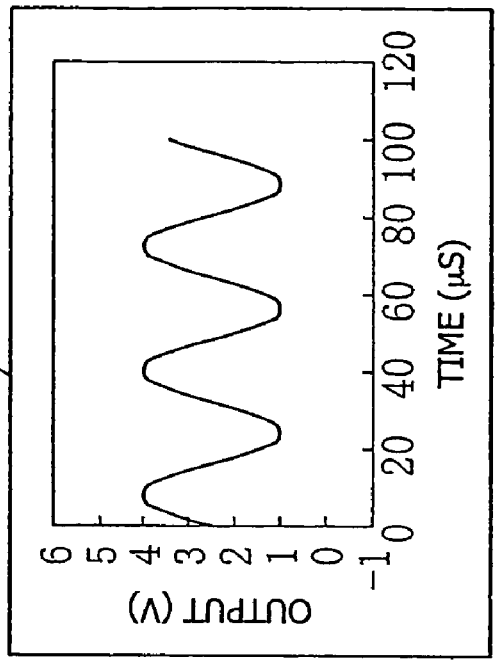
GRAPH A
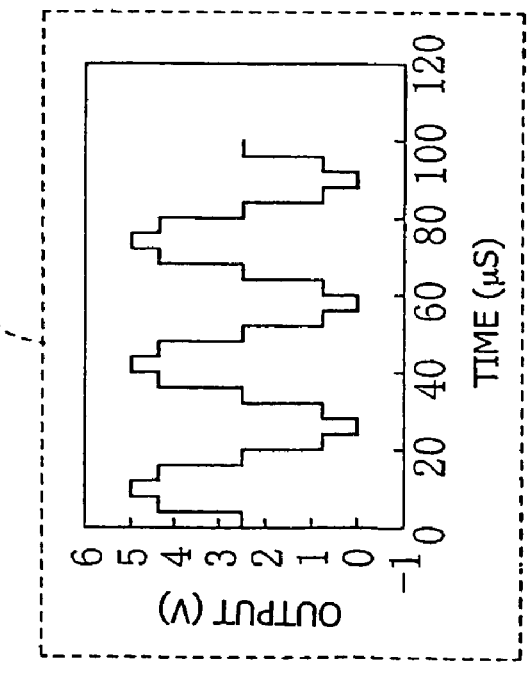
GRAPH B
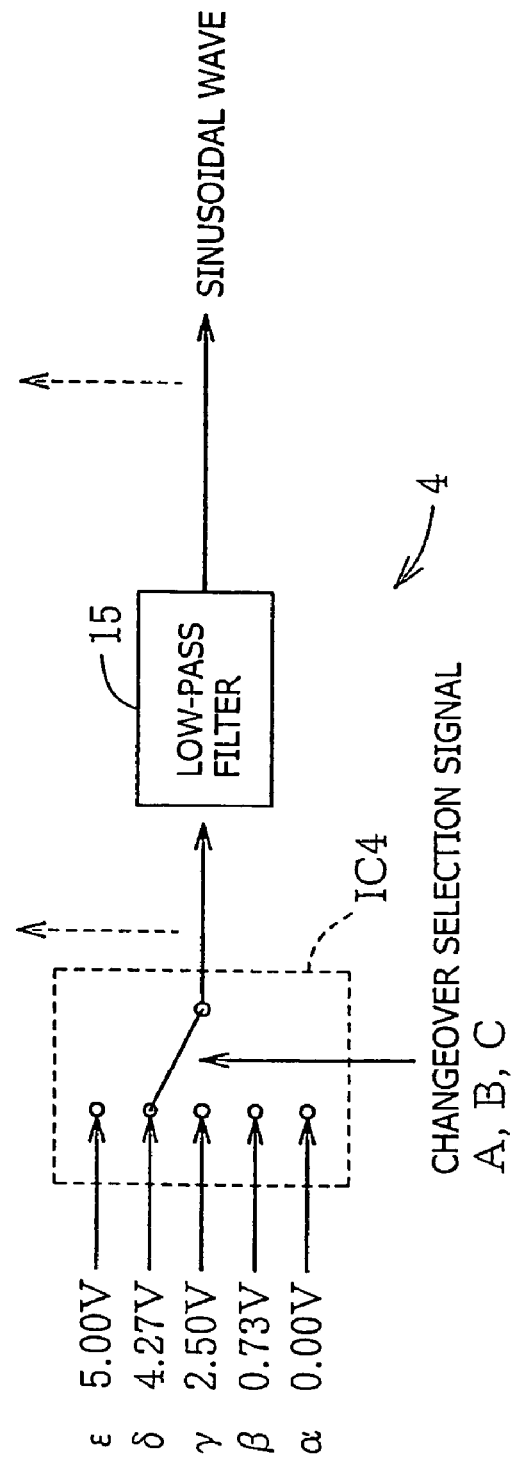

FIG. 10A
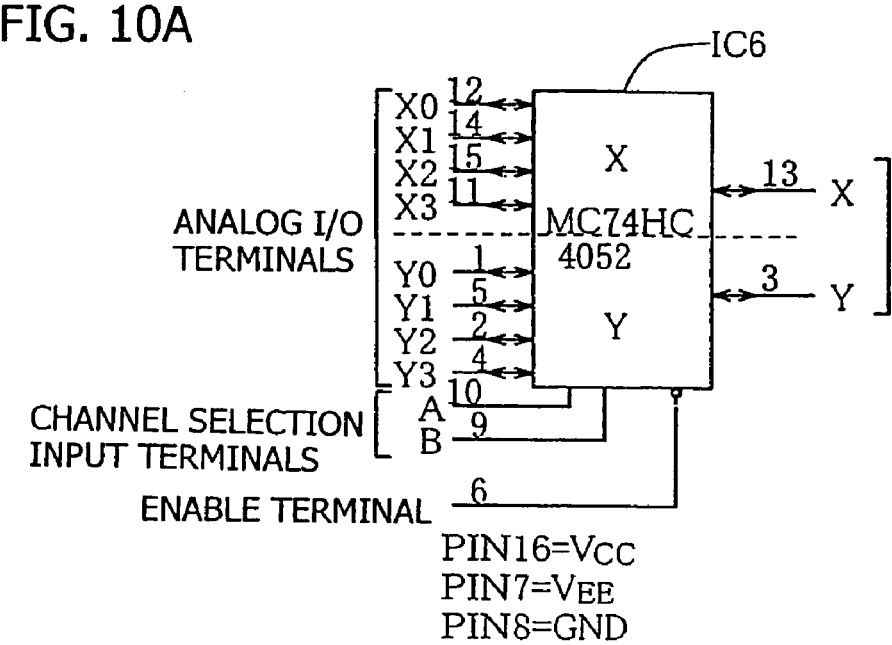
FIG. 10B
|  CONTROL INPUT  |  | CHANNEL SELECTION INPUT | TURNED-ON CHANNEL ||
| --- | --- | --- | --- | --- |
| ENABLE TERMINAL | B | A |  |  |
| L | L | L | Y0 | X0 |
| L | L | H | Y1 | X1 |
| L | H | L | Y2 | X2 |
| L | H | H | Y3 | X3 |
| H | X | X | NO ||
X = ARBITRARY
FIG. 10C
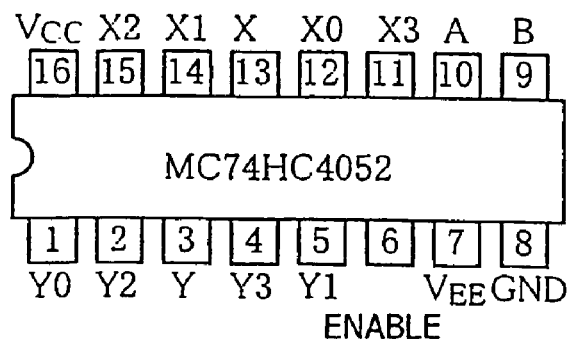

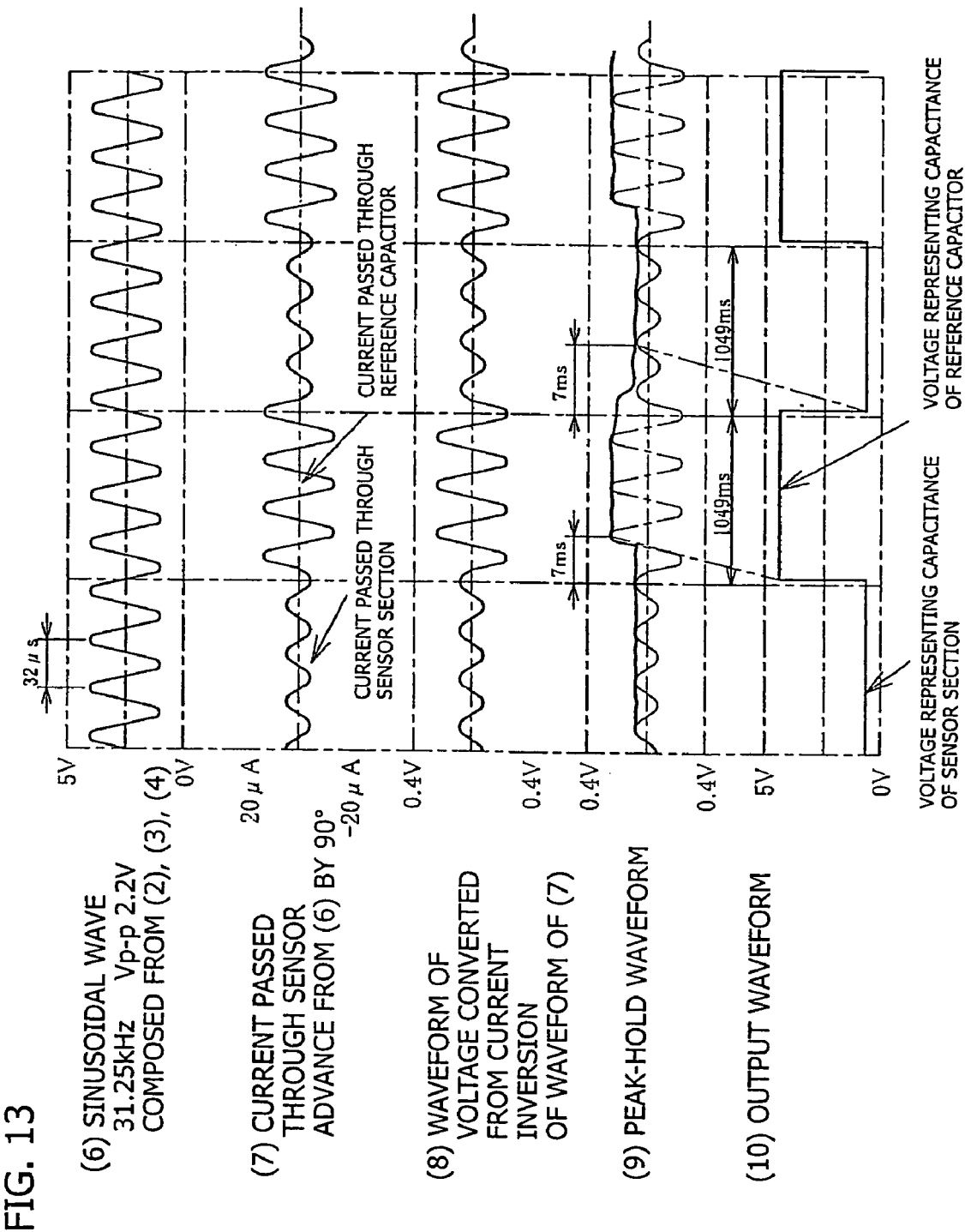

CYLINDRICAL TYPE

PLATE TYPE

OIL DETERIORATION SENSOR

TECHNICAL FIELD

The present invention relates to an oil deterioration detection apparatus.

BACKGROUND ART

Maintenance work of exchanging lubrication oil of an engine of an automobile or the like at proper timing is very important for prolonging the service life of the engine. In general, an oil gauge, which is inserted into an oil pan, is removed periodically in order to visually check the degree of contamination of the oil, whereby the person making the check can grasp the degree of deterioration of the oil. However, a driver who drives an automobile under the pressure of necessity but has no interest in the automobile, or a driver who is not mechanically inclined, generally first becomes aware of contamination of oil when a conscientious gas station attendant checks the oil. Unbelievably, some drivers change oil only at the time of automobile inspection. Although many automobiles have an oil warning indicator on their dashboard panels, the indictor merely reports the result of detection of oil level and does not report the degree of contamination.

In view of the foregoing, in Japanese Kohyo (PCT) Patent Publication No. 11-507434, Japanese Patent Application Laid-Open (kokai) No. 5-264495, Japanese Patent Application Laid-Open (kokai) No. 63-168549, and Japanese Patent Application Laid-Open (kokai) No. 59-102151, there are proposed apparatuses for detecting the degree of deterioration of engine oil by measuring the electrostatic capacitance of the oil or the dielectric constant thereof, which has a correlation with the electrostatic capacitance. One cause of oil deterioration is an increase in total acid value. This is considered to occur because base oil, which is the predominant component of the engine oil, oxidizes, with a resultant increase in the quantity of carboxylic acid and alcohol, which are polar substances. As a result, the dielectric constant of the oil increases, and the electrostatic capacitance of the oil increases accordingly. Therefore, the degree of deterioration of the oil can be known through detection of the increased electrostatic capacitance.

Incidentally, performing the above-described measurement of the electrostatic capacitance of oil requires an electric circuit for measurement purpose. The electric circuit has a pair of electrodes which are dipped in oil in a mutually facing condition and which serve as a capacitance measurement sensor. The electrodes constitute a sensing capacitor, in which oil serves as a dielectric. Basically, the capacitance of this capacitor is determined through measurement of the AC impedance of the capacitor, which measurement requires provision of peripheral circuits, including a signal generation circuit for measurement, an output processing circuit for processing a response wave signal, and other circuits. These peripheral circuits and the sensing capacitor are connected together by use of a cable such as a pair of twisted wires or a coaxial cable in order to prevent entry of noise. However, when the length of the cable is increased, the influence of parasitic capacitance of the cable itself increases, thereby preventing accurate measurement of electrostatic capacitance of oil. Therefore, for accurate measurement of electrostatic capacitance of oil, the length of the cable for connecting the sensing capacitor and the peripheral circuits must be shortened to the extent possible. As a result, the peripheral circuits must be disposed in the vicinity of the engine, to which the oil pan is attached.

In the vicinity of the operating engine, the temperature unavoidably increases even though the engine is cooled by water, and the temperature changes within a relatively wide range from atmospheric temperature to about 130° C., depending on the operating conditions. Therefore, the temperature of the peripheral circuits for measurement disposed near then engine also changes accordingly. As a result, even when the degree of deterioration of oil is not changed, the level of the detection output changes if the temperature of the peripheral circuits used for measurement changes. Further, because of long-term exposure to such high temperature, the characteristics of the peripheral circuits deteriorate to some degree, whereby the level of the detection output changes to no small extent. Both the temperature change and the long-term deterioration of the circuit characteristic lead to the problem that accurate measurement of electrostatic capacitance becomes impossible.

An object of the present invention is to provide an oil deterioration detection apparatus which can always perform accurate detection of deterioration of oil on the basis of electrostatic capacitance of the oil, even when the temperature of a circuit system for measuring the electrostatic capacitance of the oil changes.

DISCLOSURE OF THE INVENTION

In order to solve the above-described problems, the present invention provides an oil deterioration detection apparatus which includes a sensing capacitor formed of paired electrodes dipped into oil whose deterioration is to be detected and which detects deterioration of the oil on the basis of a change in electrostatic capacitance of the sensing capacitor, the apparatus comprising a measurement signal generation circuit for generating a measurement signal to be supplied to the sensing capacitor in order to measure the electrostatic capacitance of the sensing capacitor; a detection signal output circuit for outputting a detection signal on the basis of a response wave signal produced from the sensing capacitor in response to supply of the measurement signal thereto, the detection signal reflecting the electrostatic capacitance of the sensing capacitor; and an output compensation mechanism for compensating the detection signal for an output level change stemming from a temperature characteristic and/or a time-course deterioration of the detection signal output circuit.

In the above-described configuration, there is provided an output compensation mechanism for compensating for a level change of the detection signal stemming from the temperature characteristic and/or time-course deterioration of the detection signal output circuit. Accordingly, even when the temperature of the measurement circuit system including the detection signal output circuit varies because of deposition in the vicinity of an object (an engine in the case of an automobile or the like) to be lubricated by oil, the deterioration detection on the basis of the electrostatic capacitance of the oil to be measured can always be performed accurately. Further, even when the characteristics of the measurement circuit system including the detection signal output circuit deteriorate with time because of exposure to high temperature, the detection of oil deterioration can be performed accurately by use of the above-described output compensation mechanism.

Notably, oil to which the present invention is applied is mainly engine oil for automobiles; however, the present invention can be applied to other types of oil such as lubrication oil for machines.

The output compensation mechanism for compensating for a level change of the detection signal stemming from the temperature characteristic of the detection signal output circuit preferably includes a reference element whose impedance temperature coefficient is smaller than that of the sensing capacitor; and an output compensation processing circuit for performing a process of compensating the electrostatic capacitance detection signal on the basis of a measured impedance of the reference element. Even when the detected impedance of the sensing capacitor itself changes as a result of the temperature characteristic or time-course deterioration of the detection signal output circuit, such a change can be compensated for. That is, the electrostatic capacitance (impedance) of the reference element is measured every time such a change occurs, so as to normalize the detected electrostatic capacitance of the sensing capacitor, while the impedance of the reference element that has small temperature dependency or small time-course deterioration is used as a reference, whereby the influence of the temperature change and time-course deterioration can be mitigated effectively.

The reference element may be a reference capacitor. In this case, the output compensation processing circuit measures the electrostatic capacitance of the reference capacitor through impedance measurement. Use of such a reference capacitor enables particularly accurate performance of output compensation processing for correcting the electrostatic capacitance detection signal.

Notably, when a reference capacitor is used as the reference element, the reference capacitor desirably has an electrostatic capacitance temperature coefficient smaller than that of the sensing capacitor (i.e., the capacitor with the oil whose deterioration is to be detected). For example, the above-described Japanese Patent Application Laid-Open (kokai) No. 63-168549 discloses a configuration which uses a second capacitor using, as a reference medium, fresh oil of the same type as oil whose deterioration is to be detected. However, the ambient temperature of a general water-cooled automotive engine varies within the range of −30 to 120° C., and the oil, used as a reference medium, itself deteriorates (as a result of, e.g., oxidation or the like) due to influence of the ambient temperature. Therefore, the second capacitor is not at all expected to function as a reference capacitor used for output compensation of the measurement circuit system.

In the above-described configuration using a reference capacitor, the output compensation processing circuit may be configured to include a measurement signal generation circuit for generating a measurement signal to be supplied to the reference capacitor; and a detection signal output circuit for outputting a detection signal on the basis of a response wave signal produced from the reference element (e.g., the reference capacitor) in response to supply of the measurement signal thereto, the detection signal reflecting the impedance of the reference element (e.g., the detection signal reflecting the electrostatic capacitance of the reference capacitor). In this case, output compensation is performed on the basis of the result of comparison between measurement information regarding the electrostatic capacitance of the sensing capacitor on the basis of the detection signal and measurement information regarding the impedance (e.g., electrostatic capacitance) of the reference element (e.g., reference capacitor) on the basis of the detection signal. For example, when a parameter reflecting the absolute value of each electrostatic capacitance (hereinafter referred to as a "capacitance parameter") is used as the electrostatic capacitance measurement information, use of the ratio between the capacitance parameter of the sensing capacitor and the capacitance parameter of the reference capacitor effectively reduces the influence of the temperature characteristic of the detection signal output circuit.

In this case, when the measurement signal generation circuit and the detection signal output circuit of the output compensation processing circuit have the same specifications, these circuits are preferably shared by the sensing capacitor and the reference capacitor (reference element), although individual circuits may be provided for the sensing capacitor and the reference capacitor. This configuration not only reduces the number of components to thereby reduce cost, but also eliminates the influence of variation in temperature characteristic between the individually provided circuits, to thereby further enhance the reliability of output compensation. In this case, there is provided a changeover circuit for selectively connecting these circuits to the sensing capacitor or the reference capacitor (reference element). Further, when there is employed a changeover control mechanism for causing the changeover circuit to repeatedly perform the changeover of the circuit connection at constant intervals, the detection of oil deterioration accompanied by output compensation can be performed automatically and periodically, whereby the time for oil exchange or the like can be grasped more properly.

In consideration of the ambient temperature of a general water-cooled automotive engine varying within the range of −30° C. to 120° C., a capacitor whose electrostatic capacitance temperature coefficient is sufficiently small within the above-described temperature range is preferably used as the reference capacitor, in order to perform output compensation for measurement of electrostatic capacitance of oil more accurately. For example, when a capacitor whose electrostatic capacitance temperature coefficient is ±1% or less within the above-described temperature range is used, the temperature coefficient of the electrostatic capacitance of the reference capacitor itself can be mostly ignored as compared with a measurement value regarding the electrostatic capacitance of oil. As a result, even when the information regarding the electrostatic capacitance of the reference capacitor measured on the basis of the detection signal is used without correction, output compensation can be performed for the information regarding the measured electrostatic capacitance of the sensing capacitor without raising any problem. However, even in the case of a capacitor whose electrostatic capacitance temperature coefficient deviates from the above-described range, when the temperature dependency of electrostatic capacitance is known, such a capacitor can be used as the reference capacitor, so long as the information regarding the measured electrostatic capacitance of the reference capacitor is corrected for temperature on the basis of the result of temperature measurement performed by use of a temperature sensor.

In the case where compensation of time-course deterioration of the measurement circuit system including the detection signal output circuit is desired, if the electrostatic capacitance of the reference capacitor changes greatly with time along with the measurement circuit system, the reference capacitor is not expected to function as an element for compensation. Accordingly, a capacitor whose electrostatic capacitance changes with time to a small degree is preferably used as the reference capacitor. When the apparatus is applied to the above-described water-cooled automotive engine, a capacitor which has an electrostatic capacitance change rate of ±1% or less, as determined by a test (accelerated test) in which the capacitor is left at 150° C. for 240 hours, is preferably used, in order to perform output compensation for measurement of electrostatic capacitance of oil more accurately.

Next, in the present invention, a circuit which produces a sinusoidal signal as a measurement signal is preferably used as the measurement signal generation circuit. In principle, the measurement signal may assume any waveform, insofar as the measurement signal enables AC impedance measurement. For example, the measurement signal may assume a rectangular waveform, a triangular waveform, or a sawtooth waveform. However, when the measurement signal assumes a sinusoidal waveform, changes in waveform stemming from a transient phenomenon at the time of passage through a capacitor include only constant phase advance and amplitude change, and the amplitude changes generally in proportion to the electrostatic capacitance. Therefore, the processing of calculating the electrostatic capacitance from the waveform can be simplified. In this case, the detection signal output circuit is configured to output, as a detection signal, the peak value (or amplitude) of the waveform of a response wave signal generated as a result of application of the sinusoidal signal.

The measurement signal generation circuit may be configured by use of any of various oscillation circuits whose oscillation section is formed by passive elements such as R, L, and C, and an active element such as an operational amplifier. However, such an oscillation circuit has the following problem. Since a resonance-induced waveform is used as is, when the characteristics of the elements forming the oscillation section change with temperature, the influence of the characteristic change appears, while being amplified, during oscillation. Accordingly, the amplitude of an obtained waveform easily changes with temperature. Further, when a temperature compensation circuit for preventing such amplitude change is incorporated, the cost of the apparatus increases. In view of the above, the measurement signal generation circuit is configured as follows, whereby a signal waveform having a stable amplitude can be obtained by a simple circuit configuration. That is, the measurement signal generation circuit is configured to include a voltage output section for selecting and outputting one of a plurality of analog set voltages; and a voltage output control section for controlling the voltage output of the voltage output section in such a manner that the plurality of analog set voltages are selected and output in a predetermined sequence and at predetermined intervals in order to produce a stepped voltage output. In this configuration, since a waveform is generated through changeover of a plurality of analog set voltages, an analog waveform can be obtained directly. When the changes in analog set voltages with temperature can be reduced to some degree, there can be easily obtained a signal waveform having a constant amplitude which is less likely to be influenced by temperature change, because, unlike the case of a signal generator using an oscillator and an amplifier, the influence of temperature change does not appear in an amplified manner. In this case, the voltage signal obtained directly from the voltage output port of the analog switch circuit always has a stepped waveform. Therefore, when acquisition of a curved waveform such as sinusoidal waveform is desired, a low-pass filter circuit is provided in order to smooth the stepped waveform. For example, a smooth sinusoidal waveform can be easily obtained by smoothing the above-mentioned stepped waveform that flows along a sinusoidal locus, by use of a low-pass filter circuit.

Specifically, the measurement signal generation circuit may be configured to include an analog switch circuit having a plurality of voltage input ports supplied with respective constant analog set voltages, a voltage output port for selectively outputting one of the plurality of analog set voltages supplied to the voltage input ports, and a changeover circuit for selecting an analog set voltage to be output to the voltage output port on the basis of a changeover selection signal supplied from the outside; and a changeover selection signal output circuit which serves as the voltage output control section and which outputs a changeover selection signal to the analog switch circuit such that the plurality of analog set voltages are selectively output from the analog switch circuit in a predetermined sequence. A stepped waveform produced by selective output of the analog set voltages in accordance with the output sequence of the changeover selection signal is output, as a signal waveform, from the voltage output port of the analog switch circuit.

In this configuration, respective constant analog set voltages are supplied to the plurality of voltage input ports of the analog switch circuit; and the plurality of analog set voltages are selectively output to the voltage output port in a predetermined sequence by means of the changeover selection signal supplied from the outside. Thus, a stepped waveform produced by selective output of the analog set voltages in accordance with the output sequence of the changeover selection signal can be output as a signal waveform. In this configuration, since the analog set voltages are supplied directly to the analog switch circuit and are selectively output to thereby produce a waveform, an analog waveform can be obtained directly. Since the main portion is constituted by an analog switch circuit and incorporation of a compensation circuit is not required, the entire circuit can be formed at low cost.

In the above-described measurement signal generation circuit, the greater the number of input analog set voltages which the analog switch circuit can selectively output, the greater the number of steps of a waveform produced through selective output of the analog set voltages, whereby a more precise waveform can be generated. In this case, the analog set voltages supplied to the plurality of voltage input ports of the analog switch circuit are preferably generated by stepping down a power supply voltage by use of voltage division circuits. In this case, even when the number of input analog set voltages increases, such an increased number of input analog set voltages can be generated from a single power supply voltage by use of a plurality of voltage division circuits, whereby the apparatus can be configured at lower cost. The plurality of voltage division circuits may be formed by means of resistor voltage division using resistors, or capacitance voltage division using capacitors. By selecting the respective voltage division ratios of the voltage division circuits, various analog set voltages can be easily obtained from the power supply voltage. In this case, the plurality of voltage division circuits are preferably connected in parallel with one another, and receive the power supply voltage from a single power supply section. In this case, only a single power supply circuit is required, whereby the apparatus can be configured at lower cost.

The above-described measurement signal generation circuit may be configured to include an oscillation circuit whose oscillation section is formed by use of a ceramic oscillator or a quartz oscillator. Further, the changeover selection signal output circuit may be configured to selectively output the plurality of analog set voltages at changeover timings of constant intervals, which are determined on the basis of the oscillation frequency of the oscillation circuit, in order to obtain a signal waveform which includes a repeated, stepped signal waveform unit formed through output of three or more analog set voltages in a fixed sequence. For generation of a precise waveform, an important consideration is to increase the number of input analog set voltages, and secure the interval and accuracy of their changeover timings. In the above-described configuration, since the changeover timings are determined on the basis of oscillation pulses from a precision oscillation circuit including a ceramic oscillator or quartz oscillator, despite the simple configuration, a waveform accuracy comparable to that of a digital function generator can be attained, and change in the oscillation frequency with time can be reduced. Use of a quartz oscillator having a higher oscillation accuracy is advantageously used when particularly high accuracy is required. In contrast, when a ceramic oscillator (e.g., ceralock (product name)) is used, the circuit can be configured inexpensively, although the oscillation accuracy is lower than that of the quartz oscillator.

The signal waveform generated by the above-described measurement signal generation circuit may include a repeated, stepped signal waveform unit formed through output of three or more analog set voltages in a fixed sequence. This configuration is preferable for obtaining a periodic waveform, which serves as a source of a sinusoidal waveform, a rectangular waveform, or a sawtooth waveform. Further, the above-described waveform can be generated more easily through repeated performance of the processing of selecting the plurality of voltage input ports of the analog switch circuit in a fixed sequence.

An analog switch circuit which accepts a changeover selection signal having a plurality of bits can be used. An example of such an analog switch circuit is a commercially available analog multiplexer/deplexer (e.g., MC74HC4051 (product name) of Motorola). When such an analog switch circuit is used, the processing of selecting the plurality of voltage input ports of the analog switch circuit in a fixed sequence can be easily realized by the following configuration. That is, the changeover selection signal output circuit includes a base pulse oscillation circuit for generating base pulses of a constant frequency; and a frequency-division circuit for frequency-dividing the frequency of the base pulses so as to output, as a changeover selection signal, a plurality of pulse signals whose frequencies are related in terms of powers of 2. Meanwhile, the plurality of voltage input ports of the analog switch circuit are related to a plurality of combinations of signal levels of the individual bits of the changeover selection signal in such a manner that one-to-one correspondence is established between the voltage input ports and the combinations; and each voltage input port is enabled or opened upon establishment of the corresponding signal level combination, whereby the analog set voltage input to the voltage input port is output to the voltage output port. The plurality of pulse signals, which constitute the changeover selection signal, repeatedly establish the plurality of combinations of signal levels in a predetermined sequence, by virtue of differences in frequency, whereby the stepped signal waveform unit is generated and output in a manner corresponding to the sequence in which the plurality of voltage input ports are enabled.

In the analog switch circuit utilizing a changeover selection signal having a plurality of bits, since the number of combinations of bit levels of the changeover selection signal is a power of 2, in many cases, the number of the voltage input ports is also a power of 2, in order to correspond to the number of combinations of bit levels (e.g., in the case of the above-mentioned MC74CH4051, the changeover selection signal has three bits, and the number of the voltage input ports is $2^3=8$). In this case, use of a combination of pulse signals whose frequencies are related in terms of powers of 2 enables changeover of the voltage input ports to be performed by full use of the changeover selection signal having a plurality of bits, thereby enabling fine waveform generation through effective use of all the voltage input ports. Notably, pulse signals which satisfy the above-described frequency relation can be easily generated by use of a frequency-division circuit using a binary counter or the like.

Meanwhile, the voltage output control section may be configured by use of a CPU. This configuration has an advantage in that changes in specifications such as the waveform, frequency, and phase of the measurement signal can be easily coped through modification of a program or the like.

The measurement signal preferably has a frequency that is not lower than 10 kHz but is lower than 100 MHz. When the frequency of the measurement signal is lower than 10 kHz, the following problem occurs. Under the influence of a parasitic, equivalent parallel resistor stemming from a drop in insulating resistance of oil caused by deterioration thereof, the frequency of the measurement signal decreases, whereby the conductance component arising from the equivalent parallel resistor increases in relation to the susceptance component ($2\pi fC$) reflecting the electrostatic capacitance. As a result, the temperature dependency of the detection signal level increases, and the detection signal becomes likely to be easily influenced by a drop in insulating resistance of oil caused by increased oil temperature, thereby rendering proper deterioration detection difficult. Meanwhile, when the frequency of the measurement signal exceeds 100 MHz, the capacitive reactance component decreases considerably. As a result, the difference between the detection signal level for deteriorated oil and that for fresh oil decreases, thus rendering the determination for deterioration detection difficult. Further, a signal generator which can generate an accurate sinusoidal measurement signal having a frequency higher than 100 MHz is generally expensive, as is a detection circuit therefor, resulting in an increase in apparatus cost. The frequency of a sinusoidal measurement signal to be used is preferably adjusted within the range of 20 kHz to 1 MHz, more preferably within the range of 20 kHz to 50 kHz.

BRIEF DESCRIPTION OF DRAWINGS

FIG. 3A is a first explanatory diagram showing an example analog switch circuit used in the apparatus of FIG. 1.

FIG. 3B is a second explanatory diagram showing the example analog switch circuit used in the apparatus of FIG. 1.

FIG. 3C is a third explanatory diagram showing the example analog switch circuit used in the apparatus of FIG. 1.

FIG. 7A is a first explanatory diagram showing operation of the waveform generation section of FIG. 2.

FIG. 7B is a second explanatory diagram showing operation of the waveform generation section of FIG. 2.

FIG. 7C is a third explanatory diagram showing operation of the waveform generation section of FIG. 2.

FIG. 8 is an explanatory diagram showing operation of the waveform generation section of FIG. 2.

FIG. 10A is a first explanatory diagram showing an example analog switch circuit used in the changeover circuit of the output compensation processing circuit of the detection signal output circuit of FIG. 9.

FIG. 10B is a second explanatory diagram showing the example analog switch circuit.

FIG. 10C is a third explanatory diagram showing the example analog switch circuit.

FIG. 13 is a waveform diagram showing operations of different portions of the detection signal output circuit of FIG. 9.

BEST MODE FOR CARRYING OUT THE INVENTION

The best mode for carrying out the present invention will now be described with reference to the drawings.

(First Embodiment)

Figure 1:
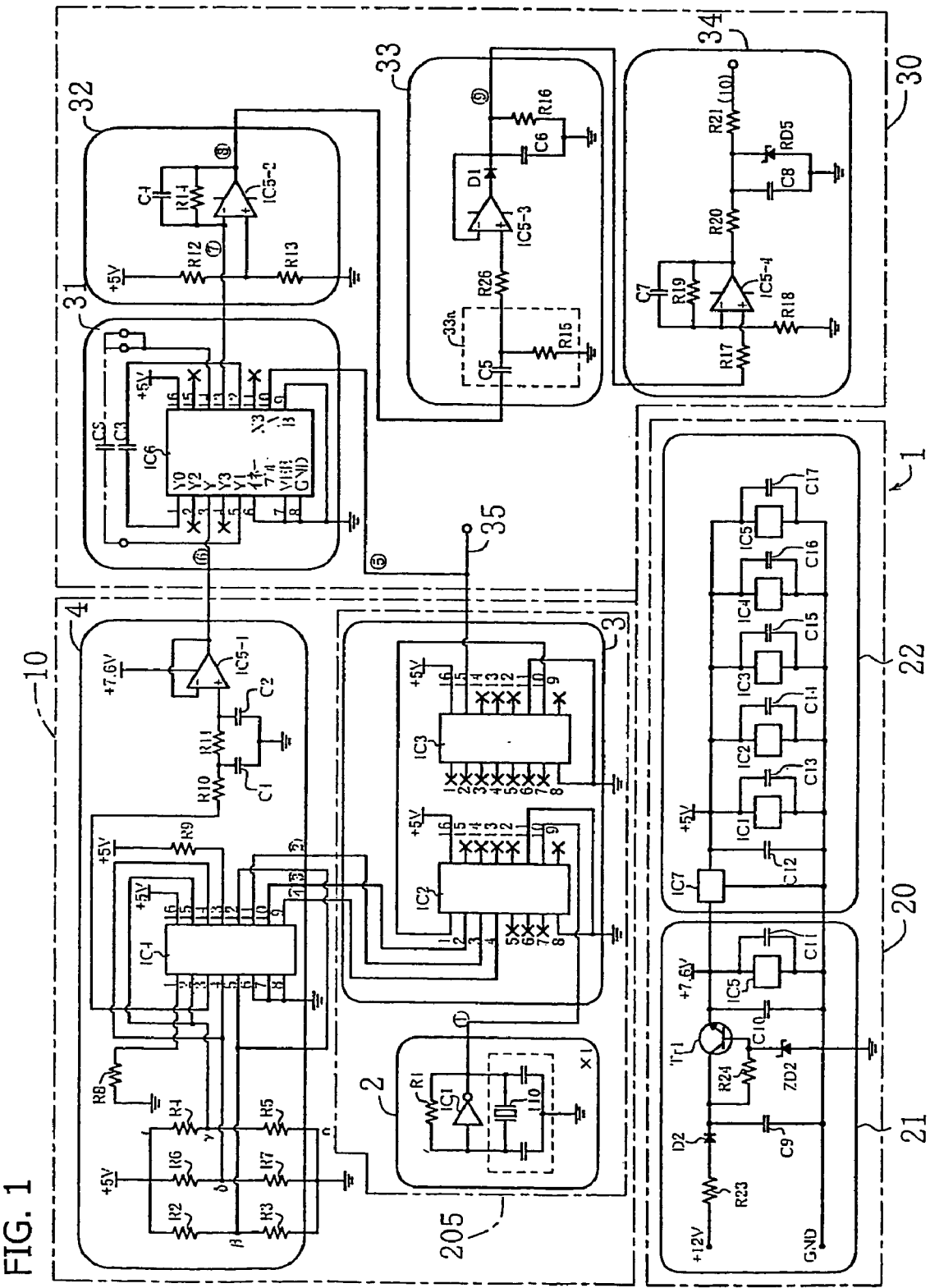
FIG. 1 is a circuit diagram showing the overall configuration of an example of an engine oil deterioration detection apparatus according to a first embodiment of the present embodiment.
Figure 14A:
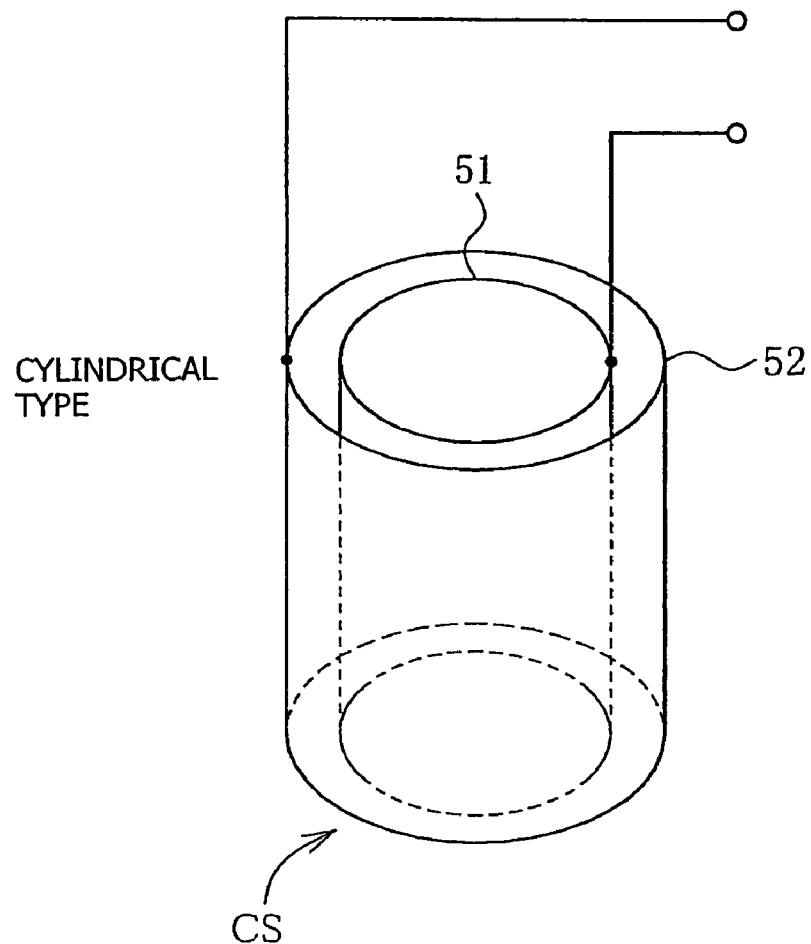
FIG. 14A is a schematic diagram showing an example configuration of a sensing capacitor.
Figure 14B:
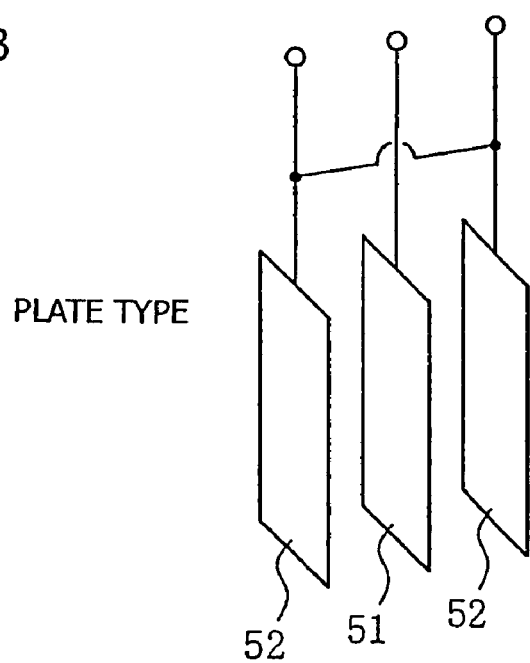
FIG. 14B is a schematic diagram showing another example configuration of the sensing capacitor.

FIG. 1 is an overall circuit diagram showing one embodiment of an engine oil deterioration detection apparatus according to the present embodiment. The engine oil deterioration detection apparatus 1 mainly consists of three circuits; i.e., a measurement signal generation circuit 10, a detection signal output circuit 30, and a power supply circuit 20. As already described, the basic function of the engine oil deterioration detection apparatus 1 is to detect deterioration of engine oil on the basis of a change in electrostatic capacitance of a sensing capacitor CS shown in FIG. 14, which is formed by paired electrodes 51 and 52 and is dipped into the engine oil whose deterioration is to be detected. In the embodiment of FIG. 14A, the electrodes 51 and 52 of the sensing capacitor CS assume cylindrical shapes and are disposed coaxially. When the sensing capacitor is placed in oil, the oil enters the clearance between the electrodes 51 and 52, whereby a capacitor is formed with the oil serving as a dielectric. Alternatively, as shown in FIG. 14B, the paired electrodes 51 and 52 may be formed by parallel electrode plates. In this embodiment, one electrode is formed by the two electrode plates 52 which are electrically connected together via a connection wire. In the present embodiment, the term "paired electrodes" refers to electrodes which are charged in different polarities when a direct current voltage is applied to the electrodes. Each of the electrodes may be formed of a single electrode plate as shown in FIG. 14A, or either one or both of the electrodes may be divided into a plurality of electrode pieces as shown in FIG. 14B.

Referring back to FIG. 1, the measurement signal generation circuit 10 is configured to generate a measurement signal (6) to be input to the sensing capacitor CS in order to measure the electrostatic capacitance of the sensing capacitor CS. Specifically, the measurement signal generation circuit 10 includes a waveform generator 4 mainly consisting of an analog switch circuit IC4; and a changeover selection signal output circuit 205 which supplies a changeover selection signal to the waveform generator 4. In the present embodiment, an 8-channel analog multiplexer/demultiplexer MC74HC4051 (product of Motorola, USA) is used for the analog switch circuit IC4. FIGS. 3A to 3C show the details of the analog switch circuit IC4, wherein FIG. 3A shows its terminal configuration, FIG. 3B shows its operation table, and FIG. 3C shows its external pin layout. As shown in FIG. 3A, the analog switch circuit IC4 has a plurality of (eight, in the present embodiment) voltage input ports (analog input/output terminals) X0 to X7 for receiving respective constant analog set voltages; a voltage output port (common input/output terminal) X for outputting a selected one of the plurality of analog set voltages input to the voltage input ports X0 to X7; and input sections (channel selection input terminals) A, B, C for receiving a changeover selection signal (3 bits) supplied externally. The analog switch circuit IC4 is configured to select an analog set voltage on the basis of the changeover selection signal and to output the selected analog set voltage to the voltage output port X.

In accordance with the combination of input voltage levels (a level higher than a threshold is represented by H, and a level lower than the threshold is represented by L) of an enable signal terminal and the channel selection input terminals A, B, and C; i.e., in accordance with the operation table of FIG. 3B, one of the channels corresponding to the analog input terminals X0 to X7 is activated, whereby the analog set voltage input to the activated channel is allowed to be selectively output to the common input/output terminal X.

Figure 2:
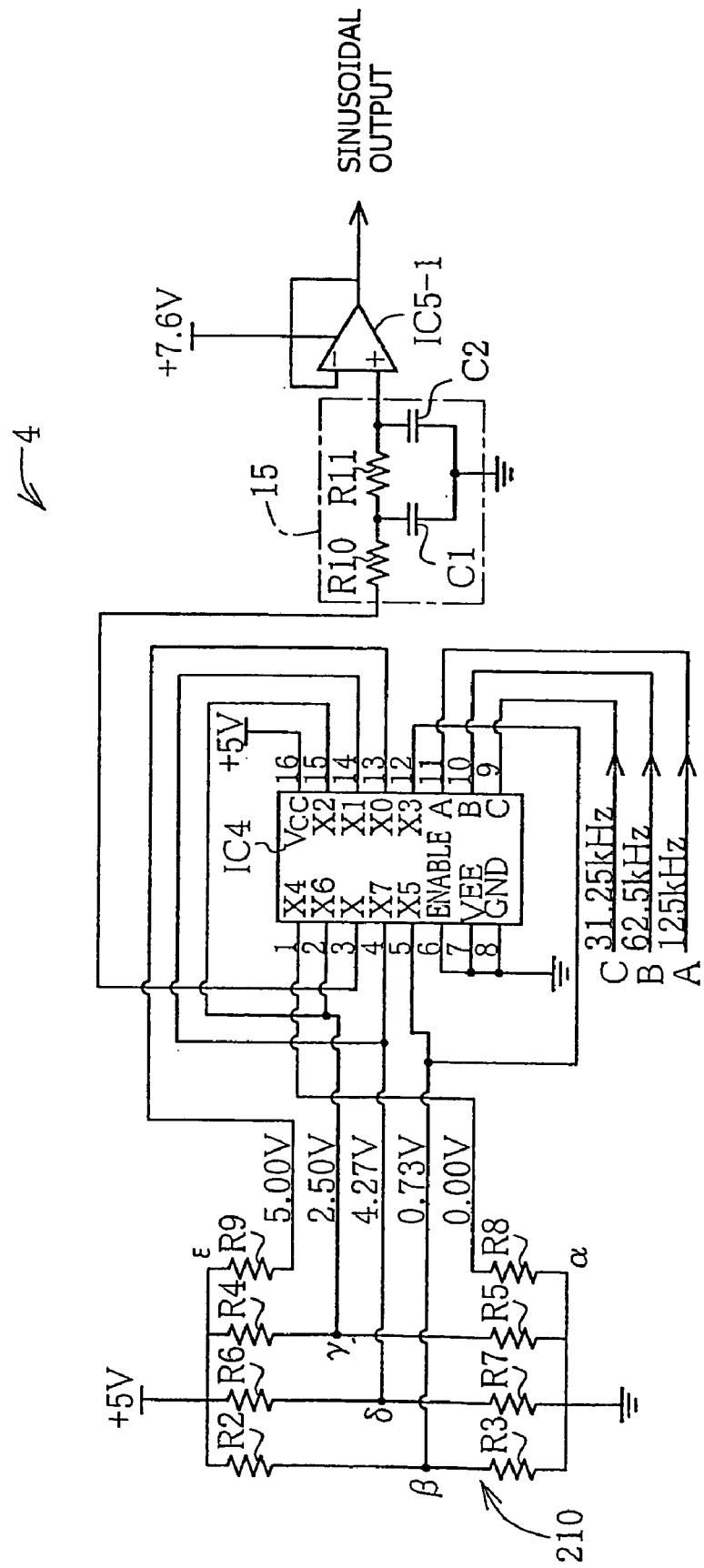
FIG. 2 is a circuit diagram showing an example of the waveform generation section of the apparatus of FIG. 1.

FIG. 2 shows the waveform generation section 4 in an enlarged manner. A set voltage generation circuit 210 is provided in a stage preceding the analog switch circuit IC4. The set voltage generation circuit 210 includes a plurality of voltage division circuits which generate a plurality of different set voltages β (0.73 V), γ (2.50 V), δ (4.27 V) by stepping down a power supply voltage (+5 V) by use of respective pairs of voltage division resistances (R2, R3), (R4, R5), and (R6, R7). Further, a pull-up resistor R9 and a pull-down resistor R8 are provided in order to output the ground level voltage α and the power supply voltage ε as a set voltage of 0 V and a set voltage of +5 V, respectively.

These set voltages form a stepped waveform which depicts a sinusoidal locus as shown in graph A of FIG. 8, when voltage-increasing changeover (α→β→γ→δ→ε) and voltage-decreasing changeover (ε→δ→γ→β→α) are alternately and continuously repeated at equal time intervals. Notably, in the graph A of FIG. 8, the changeover operation is started with the voltage-increasing changeover in such a manner that the voltage increases from γ to δ and then to ε. In this case, the intermediate set voltages β, γ, and δ between the ground level voltage α and the power supply voltage ε must be output two times per cycle; i.e., once during the voltage-increasing changeover in the regular sequence, and once during the voltage-decreasing changeover in the reverse sequence. In view of the above, as shown in FIG. 2, the intermediate set voltages β, γ, and δ are each supplied to two different sets of ports among the eight voltage input ports (analog input/output terminals) X0 to X7; and these two sets of voltage input ports are alternately used during the voltage increasing period and the voltage decreasing period, respectively. Thus, a voltage output corresponding to one wavelength of a periodic functional waveform such as a sinusoidal wave can be attained through simple sequential changeover of the voltage input ports X0 to X7.

Figure 4A:
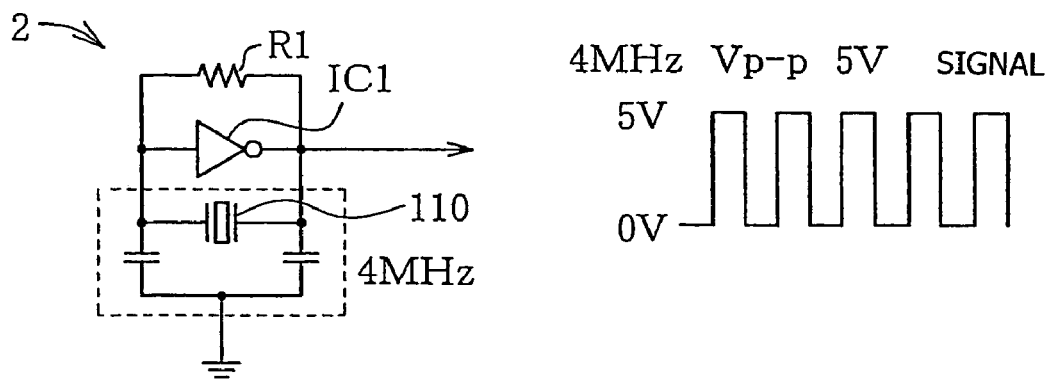
FIG. 4A is a circuit diagram showing the oscillation circuit section of FIG. 2 in an enlarged manner.
Figure 6:
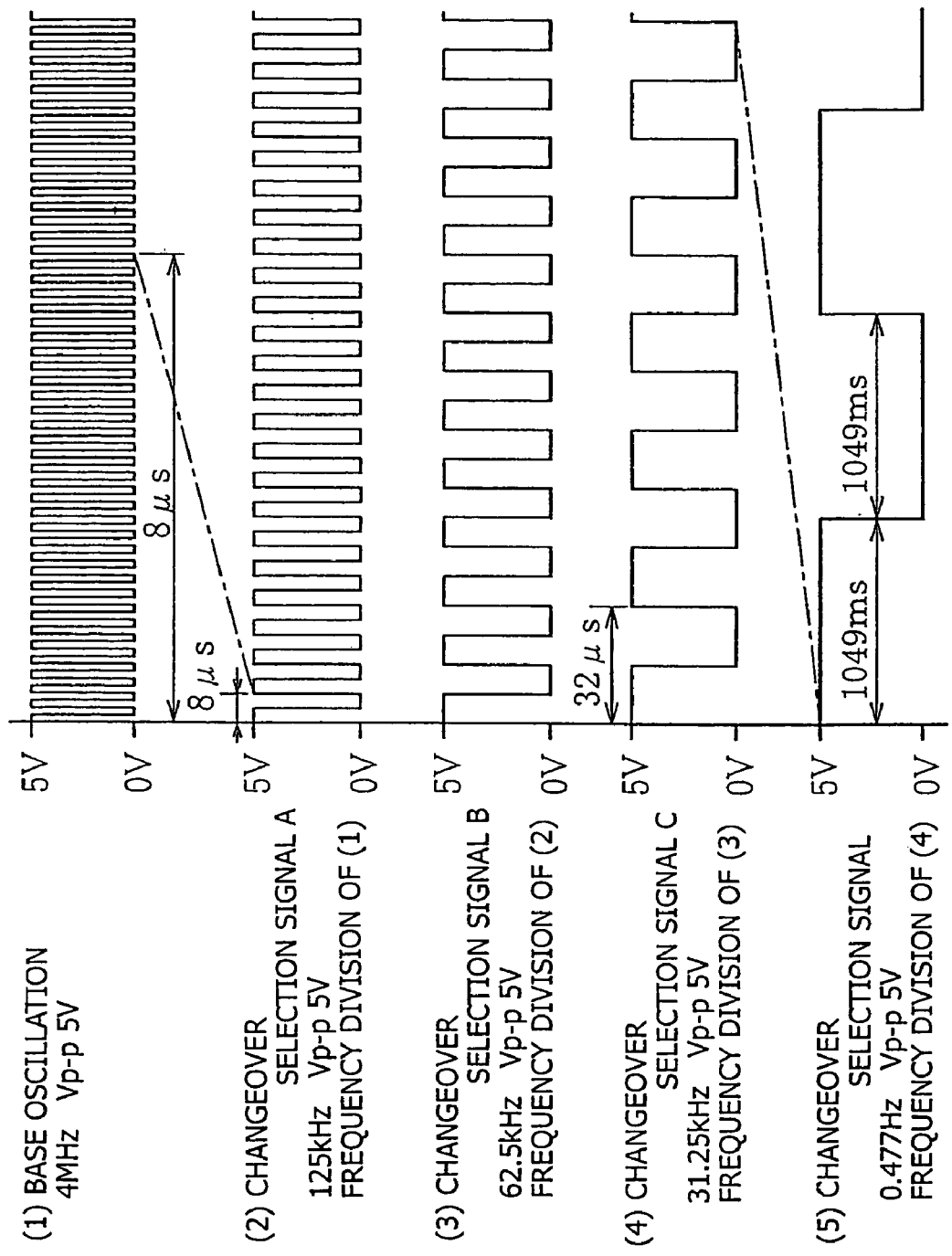
FIG. 6 is a timing chart showing example waveforms output from the frequency-division circuit of FIG. 4B.

Referring back to FIG. 1, the changeover selection signal output circuit 205 plays a role of supplying the changeover selection signal to the analog switch circuit IC4 in such a manner that the plurality of analog set voltages are output from the analog switch circuit IC4 in a predetermined sequence as described above. Specifically, the changeover selection signal output circuit 205 includes an oscillation circuit 2 whose oscillation section is formed by a ceramic oscillator 110 (e.g., ceralock (product name): a quartz oscillator may be used). As shown in FIG. 4A, the oscillation circuit 2 is a Colpitts oscillator modified such that an inductor is replaced with the ceramic oscillator 110, an inverter IC1 is used as an inverted amplification section, and a feedback resistor R1 is added. In the present embodiment, the oscillation circuit 2 is configured to output rectangular-wave clock pulses having an oscillation frequency of 4 MHz and a peak-to-peak voltage $V_{p-p}$ of 5 V corresponding to the drive voltage of the inverter IC1, as shown in FIG. 6(1).

The changeover selection signal output circuit 205 switches and outputs the changeover selection signals A, B, and C at changeover timings of constant intervals determined on the basis of the oscillation frequency of the oscillation circuit 2, in such a manner that three or more (in the present embodiment, eight) analog set voltages are output (notably, β, γ, and δ are output two times) in a fixed sequence to thereby obtain a signal waveform in which a stepped signal waveform unit is repeated. Specifically, as shown in FIG. 1, the changeover selection signal output circuit 205 includes a frequency division circuit 3 for dividing the frequency of the oscillation circuit 2, which serves as a fixed-frequency base pulse oscillator, so as to output, as a changeover selection signal, a plurality of pulse signals whose frequencies are mutually related in terms of powers of 2.

Figure 4B:
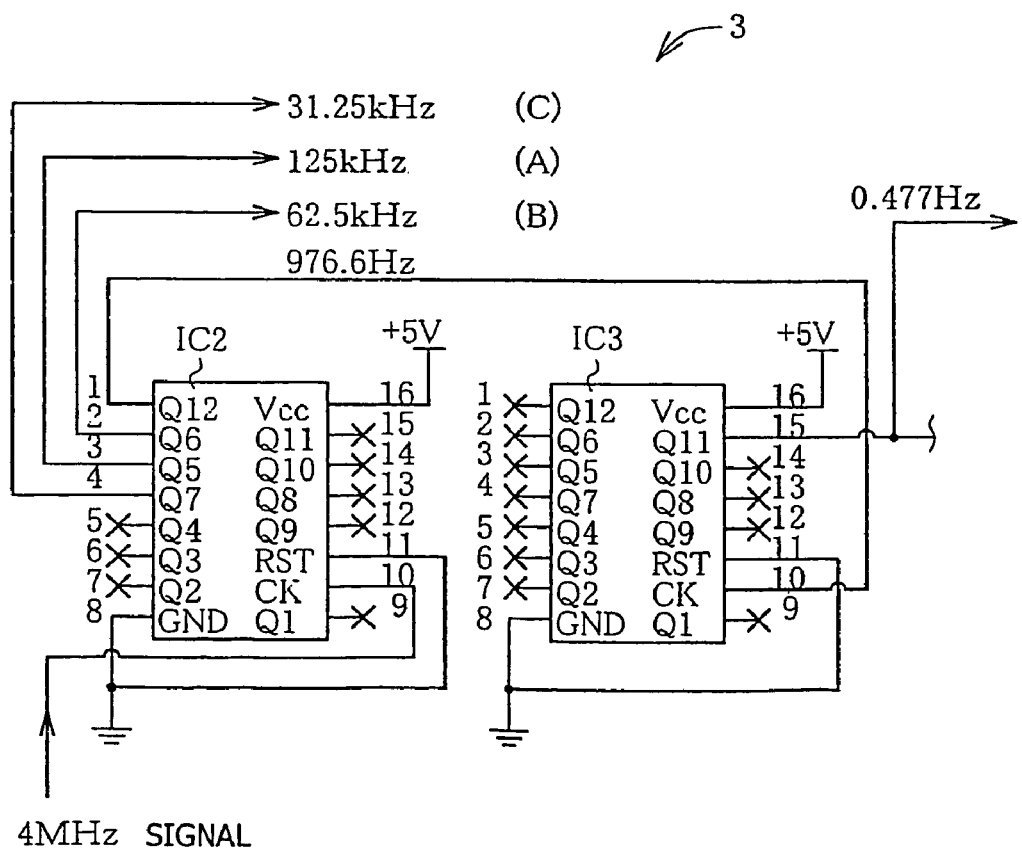
FIG. 4B is a circuit diagram showing the frequency-division circuit section of FIG. 2 in an enlarged manner.
Figure 5:
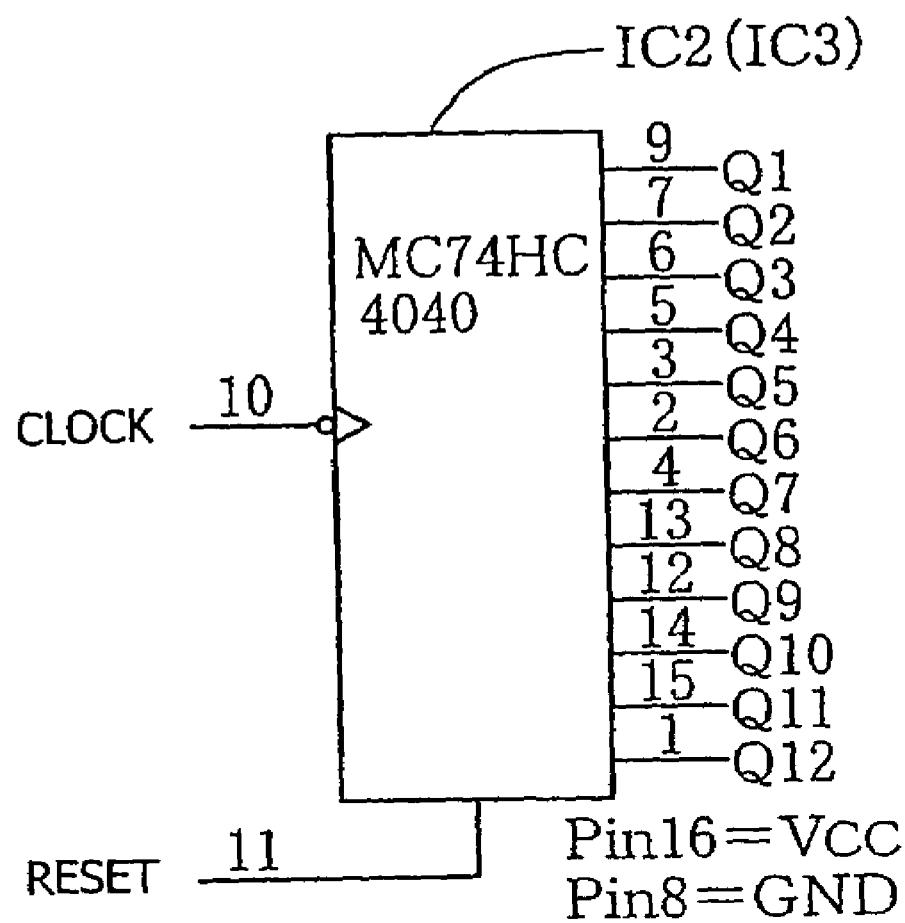
FIG. 5 is an explanatory diagram showing an example binary counter used in the frequency-division circuit of FIG. 4B.

As shown in FIG. 4B, the frequency division circuit 3 mainly consists of two binary counters IC2 and IC3. In the present embodiment, a 12-stage binary ripple counter MC74HC4040A (product of Motorola, USA) is used for the binary counters IC2 and IC3. FIG. 5 shows the details of the counter; i.e., shows its terminal configuration.

In the present embodiment, as shown in FIG. 4B, Q5 of the binary counter IC2 in the preceding stage is used as the bit A of the changeover selection signal, Q6 of the binary counter IC2 is used as the bit B of the changeover selection signal, and Q7 of the binary counter IC2 is used as the bit C of the changeover selection signal. The Q5 output for the bit A consists of a train of 125 kHz rectangular clock pulses shown in (2) of FIG. 6, as a result of the 4 MHz base pulse train shown in (1) of FIG. 6 being frequency-divided to $\frac{1}{2}^5$. Similarly, the Q6 output for the bit B consists of a train of 62.5 kHz rectangular clock pulses shown in (3) of FIG. 6, as a result of the base pulse train being frequency-divided to $\frac{1}{2}^6$; and the Q7 output for the bit C consists of a train of 31.25 kHz rectangular clock pulses shown in (4) of FIG. 6, as a result of the base pulse train being frequency-divided to $\frac{1}{2}^7$. Since these trains of rectangular clock pulses are frequency-divided outputs from the binary counter IC2, the frequencies of these pulse trains naturally satisfy the above-mentioned relation involving powers of 2. As shown in FIG. 2, these pulse trains are input to the analog switch circuit IC4 as the bits A, B, and C of the above-mentioned changeover selection signal.

Meanwhile, as shown in FIG. 4B, the Q12 output (frequency: 976.6 Hz) of the binary counter IC2 in the preceding stage is input, as base clocks, to the binary counter IC3 in the following stage, whereby frequency-divided clock pulses of 0.477 Hz ((5) in FIG. 1) are output from Q11 of the counter IC3. As will be described later, the frequency-divided clock pulses are used as a changeover control signal which defines timing for changeover between the sensing capacitor CS and a reference capacitor C3.

As shown in FIG. 3B, the plurality of voltage input ports X0 to X7 of the analog switch circuit IC4 are related to the plurality of combinations of the signal levels of the bits A, B, and C of the changeover selection signal in such a manner that one-to-one correspondence is established between the voltage input ports and the combinations. Each of the voltage input ports X0 to X7 is opened (enabled) when the corresponding combination of signal levels H and L is formed, and the analog set voltage input to the opened input port is output to the voltage output port X. Through use of the plurality of clock pulse signals that satisfy the above-described frequency relation as the bits A, B, and C of the changeover selection signal, as shown in FIG. 7B, a plurality of (in the present embodiment, $2^3=8$) combinations of signal levels H and L are repeatedly formed in a fixed sequence, because of the difference in frequency between the clock pulse signals. Specifically, within each cycle of the C bit pulse signal having the longest wavelength, eight H/L combinations are successively formed without any duplication. As a result, as shown in FIG. 7C, a stepped signal waveform unit is generated to have a profile corresponding to the sequence in which the plurality of voltage input ports X0 to X7 are opened, and the thus-generated waveform unit is output.

Referring back to FIG. 2, the waveform output from the voltage output port X of the analog switch circuit IC4 naturally assumes a stepped profile; in the present embodiment, a low-pass filter circuit 15 is provided in order to smooth the signal waveform. In the present embodiment, the low-pass filter circuit 15 is configured such that two passive filters consisting of resistors (R10, R11) and capacitors (C1, C2) are cascaded; however, the configuration of the low-pass filter circuit 15 is not limited thereto, and an active filter may be used. In the present embodiment, as shown in FIG.

8, when the signal having a stepped sinusoidal waveform (graph A)—which is output from the analog switch circuit IC4 as a result of changeover and output of the changeover selection signal (bits A, B, and C)—is passed through the low-pass filter circuit 15, a sinusoidal signal output as shown in graph B is obtained. As shown in FIG. 2, the signal (sinusoidal signal) smoothed by means of the low-pass filter circuit 15 is fed to an operational amplifier IC5-1, serving as a voltage follower, in which the smoothed signal undergoes impedance conversion. Subsequently, this smoothed signal (6) (see FIG. 13) is output as a measurement signal to be used for measurement of electrostatic capacitance.

Figure 9:
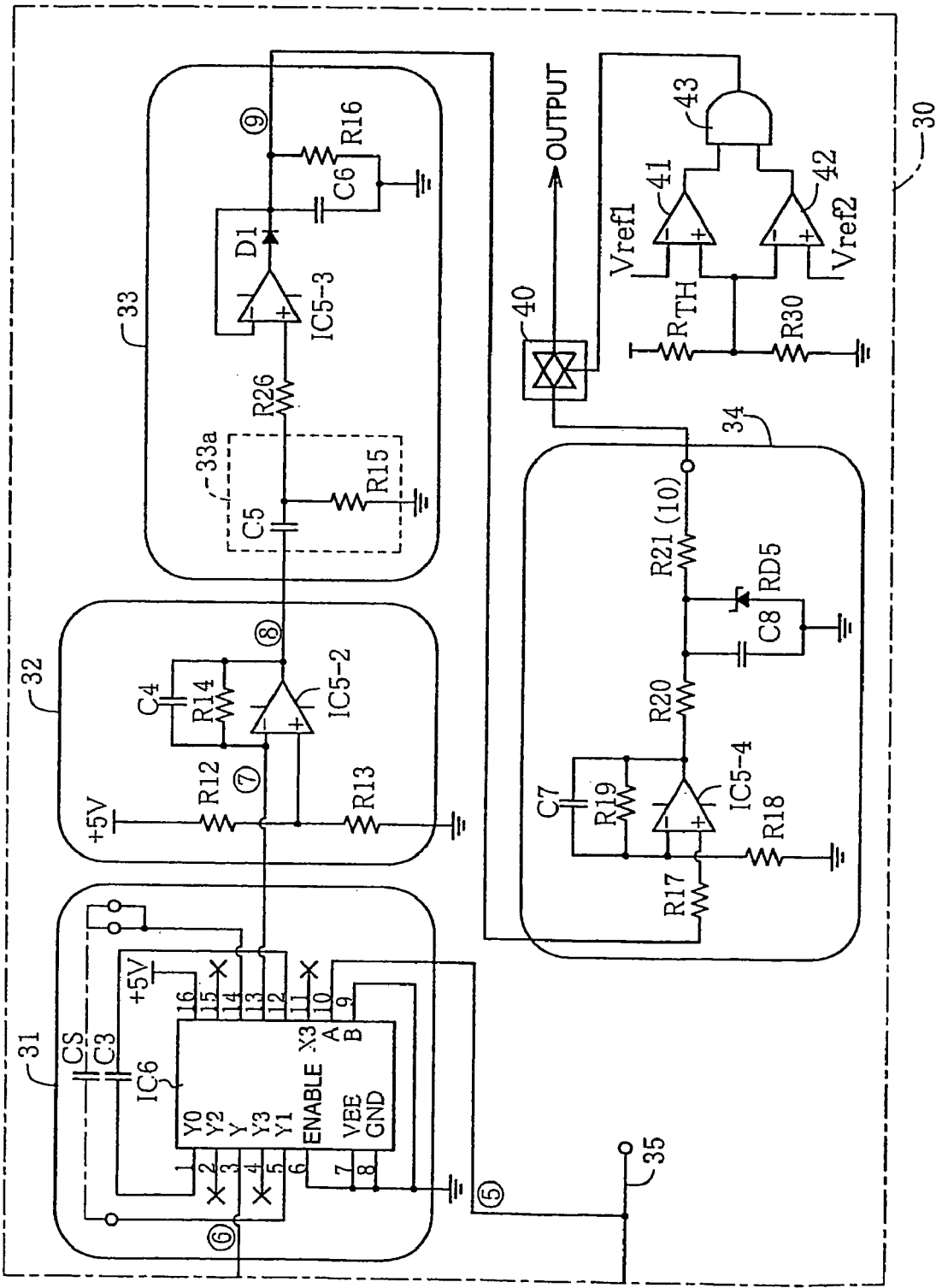
FIG. 9 is a circuit diagram showing an example of the detection signal output circuit of the apparatus of FIG. 1.

FIG. 9 shows the detection signal output circuit 30 in an enlarged manner. The detection signal output circuit 30 is configured to output a detection signal (10), which reflects the electrostatic capacitance of the sensing capacitor CS, on the basis of the response wave signal (7) which is output from the sensing capacitor CS in response to input of the measurement signal (6) thereto. The engine oil deterioration detection apparatus 1 includes an output compensation mechanism for compensating change in the output level of the detection signal (10) attributable to the temperature characteristics of the detection signal output circuit.

Specifically, the output compensation mechanism includes a reference capacitor C3 (reference element) which is smaller than the sensing capacitor CS (i.e., oil whose deterioration is to be detected) in terms of the temperature coefficient of electrostatic capacitance; and the output compensation processing circuit 31 performs processing for compensating the electrostatic capacitance detection signal on the basis of the result of measurement of the electrostatic capacitance (impedance) of the reference capacitor C3. In the present embodiment, the measurement signal generation circuit 10 and the detection signal output circuit 30 are commonly used between the sensing capacitor CS and the reference capacitor C3; and a changeover circuit IC6 is provided to selectively connect these circuits to the sensing capacitor CS or the reference capacitor C3.

The changeover circuit IC6 is formed from an analog switch circuit. In the present embodiment, an 8-channel analog multiplexer/demultiplexer MC74HC4052 (product of Motorola, USA) is used for the changeover circuit IC6. FIGS. 10A to 10C show the details of the analog switch circuit, wherein FIG. 10A shows its terminal configuration, FIG. 10B shows its operation table, and FIG. 10C shows its external pin layout. As shown in FIG. 10, the analog switch circuit has two groups of input ports X0 to X3 and Y0 to Y3, each group consisting of a plurality of voltage input ports (analog input/output terminals); voltage output ports (common input/output terminals) X and Y for respectively outputting an analog voltage selected from the plurality of analog set voltages input to the voltage input ports X0 to X3 and an analog voltage selected from the plurality of analog set voltages input to the voltage input ports Y0 to Y3; and input sections (channel selection input terminals) A and B for receiving a changeover selection signal (2 bits) supplied externally. The analog switch circuit IC6 is configured to select analog set voltages on the basis of the changeover selection signal and to output the selected analog set voltages to the voltage output ports X and Y, respectively.

In accordance with the combination of input voltage levels (a level higher than a threshold is represented by H, and a level lower than the threshold is represented by L) of an enable signal terminal and the channel selection input terminals A and B; i.e., in accordance with the operation table of FIG. 10B, one of the channels corresponding to the analog input terminals X0 to X3 and one of the channels corresponding to the analog input terminals Y0 to Y3 are activated, whereby the analog set voltages input to the respective activated channels are allowed to be selectively output to the common input/output terminals X and Y, respectively.

As shown in FIG. 9, of the channel selection input terminals A and B, the terminal B is grounded, whereby the terminal B is always maintained at the L level. Meanwhile, the changeover control signal (0.477 Hz) (5) output from the above-described frequency division circuit 3 (FIG. 1) is supplied to the terminal A, whereby the level of the terminal A is switched between the H level and the L level at constant intervals (in the present embodiment, intervals of about 1 second).

Figure 11:
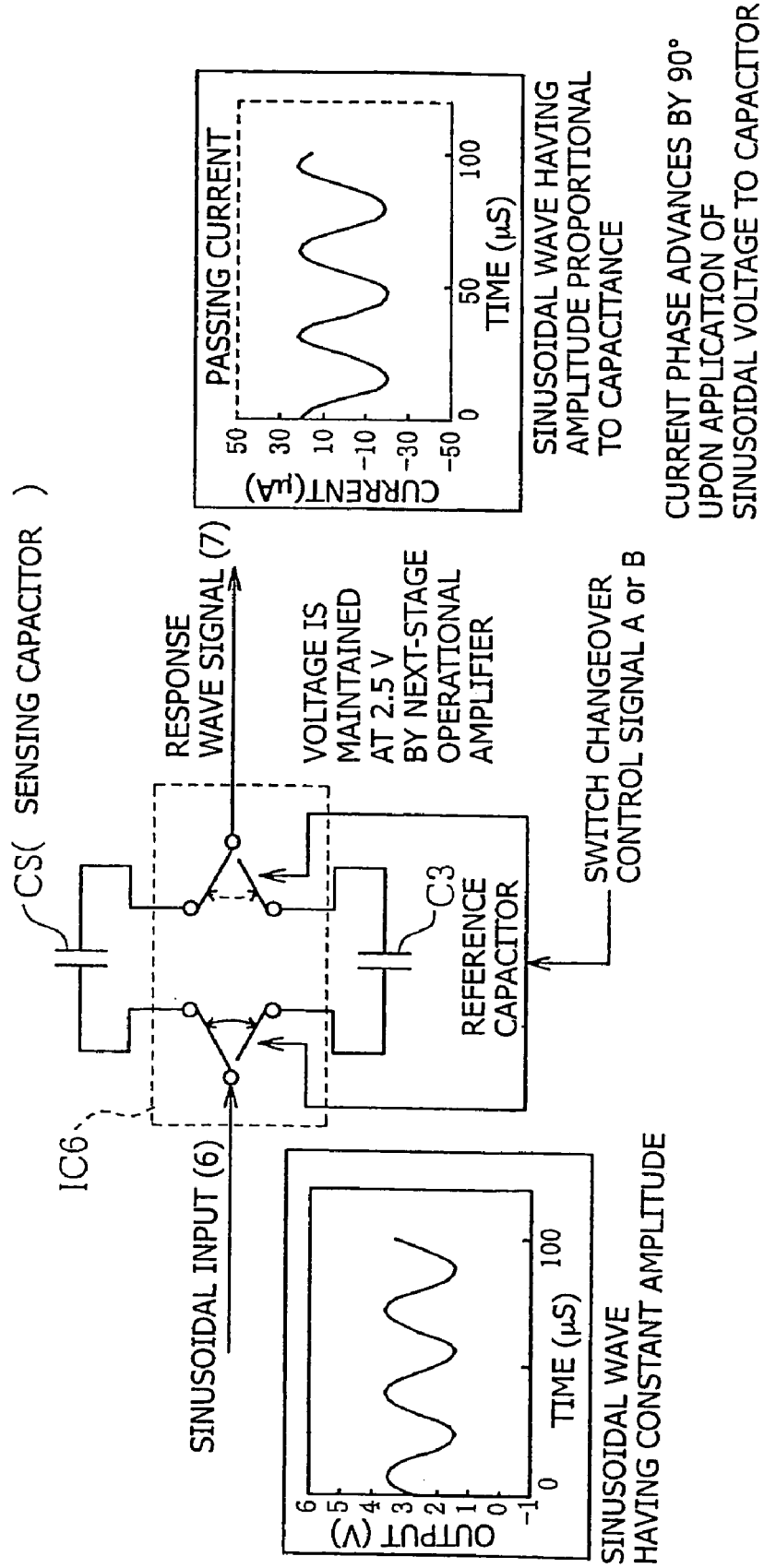
FIG. 11 is an explanatory diagram showing operation of the output compensation processing circuit.
Figure 12:
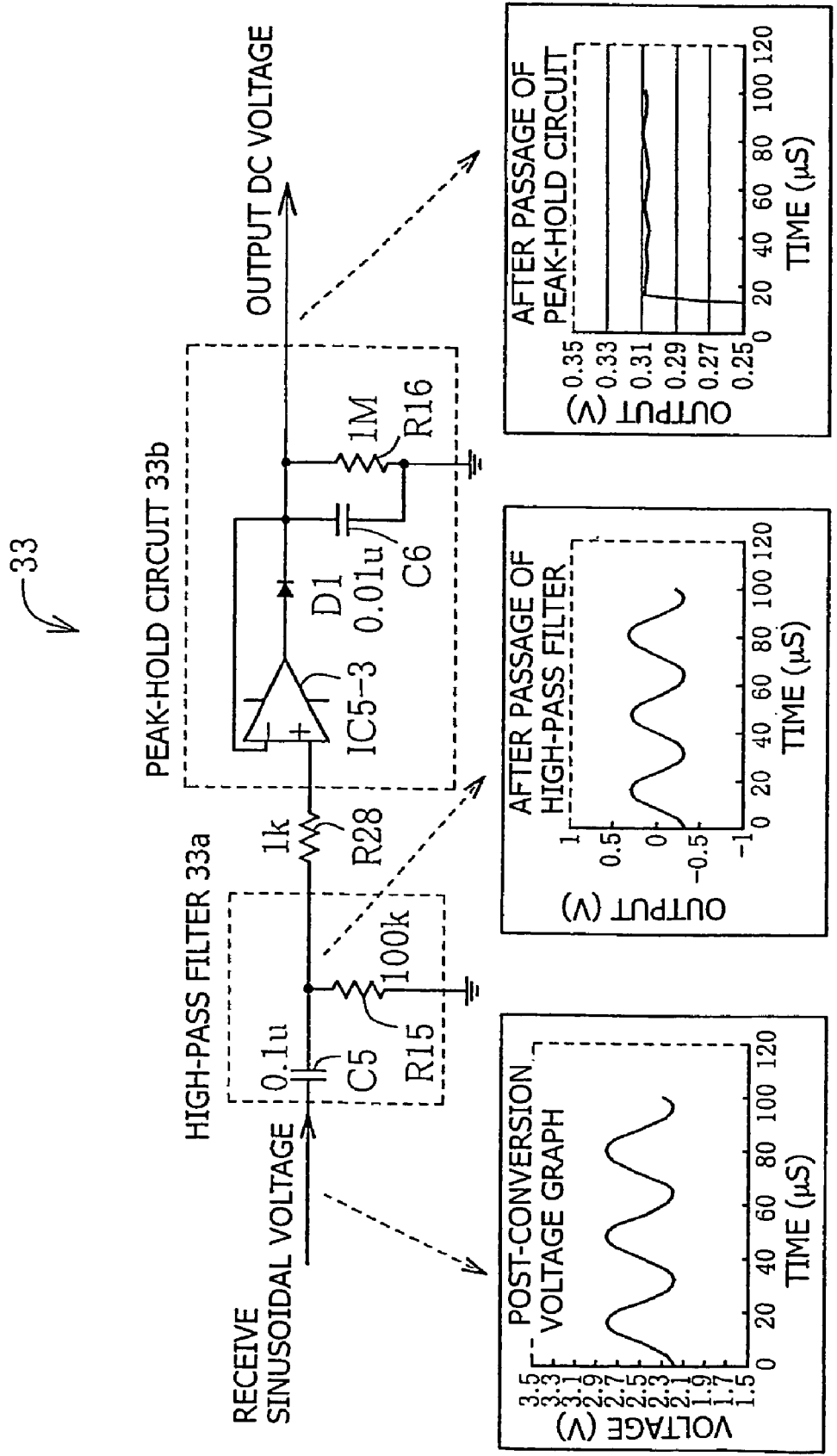
FIG. 12 is a circuit diagram showing an example configuration of the peak-hold circuit of the detection signal output circuit of FIG. 9, accompanied by graphs showing operation of the peak-hold circuit.

As shown in FIG. 10, when the level of the terminal B is L, the channels for the paired ports Y0 and X0 and the channels for the paired ports Y1 and X1 are selectively opened in response to changeover of the level of the terminal A between H and L. As shown in FIG. 9, the reference capacitor C3 is connected between the ports Y0 and X0, whereas the sensing capacitor CS is connected between the ports Y1 and X1. Meanwhile, the sinusoidal measurement signal (6) is supplied to the common input/output terminal Y, and the common input/output terminal X is used as an output-side terminal. Accordingly, through the changeover of the level of the terminal A between H and L by means of the changeover control signal (5), as shown in FIG. 11, the measurement signal (6) is alternately supplied to the reference capacitor C3 and the sensing capacitor CS at intervals of about 1 second; and the response signal (7) is output from the common input/output terminal X. That is, it is understood that the analog switching circuit IC6 shown in FIG. 9 realizes, in cooperation with the frequency division circuit 3, a function which serves as a changeover circuit and a changeover control mechanism for repeatedly performing the changeover of the circuit connections at constant intervals.

Figure 18:
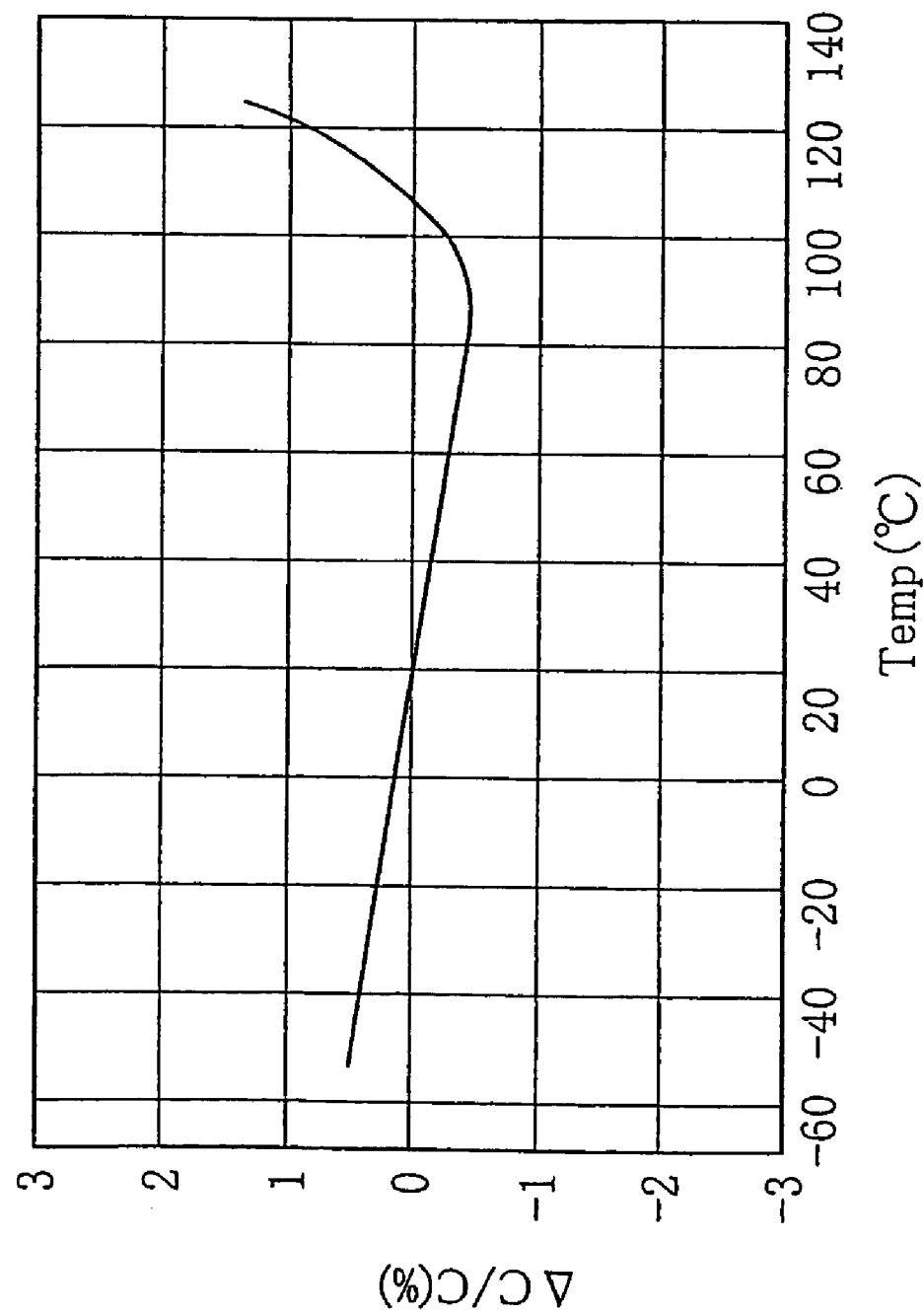
FIG. 18 is a graph showing an example of the temperature dependency of electrostatic capacitance of a reference capacitor.

The electrostatic capacitance of the reference capacitor C3 has a temperature coefficient of ±1% or less within a temperature range of −30° C. to 120° C., with the electrostatic capacitance at 20° C. serving as a reference. In the present embodiment, a plastic film capacitor (product name: ECHU (Matsushita Electric Industrial Co., Ltd.), which uses polyphenylene sulfido (PPS) resin as a dielectric, is employed as the reference capacitor C3. FIG. 18 shows the change in electrostatic capacitance of the capacitor with temperature (the vertical axis represents a rate of change in electrostatic capacitance with the electrostatic capacitance at 20° C. used as a reference).

As shown in FIG. 11, in the present embodiment, a sinusoidal signal is used as the measurement signal (6), and the detection signal output circuit outputs, as a detection signal, the peak value of a response waveform produced as a result of application of the sinusoidal signal. This will now be described in detail. As shown in FIG. 13, the original waveform of the measurement signal (6) is a sinusoidal wave having a substantially constant amplitude. However, as a result of alternate application of the measurement signal to the reference capacitor C3 and the sensing capacitor CS, in the output response wave signal (7) (current signal), a first waveform produced as a result of passage through the reference capacitor C3 and a second waveform produced as a result of passage through the sensing capacitor CS alternately appear at constant intervals. The amplitudes of the first and second waveforms increase and decrease in proportion to the electrostatic capacitances of the reference capacitor C3 and the sensing capacitor CS, respectively.

As shown in FIG. 9, the response wave signal (7) is converted to a voltage signal (8) by means of a current-voltage conversion circuit 32, which mainly consists of an operational amplifier IC5-2 and a feedback resistor R14 for current detection (see FIG. 13 (8)). Notably, in the present embodiment, the measurement signal (6) (thus, the response wave signal (7)) is generated to have an single-polarity waveform whose center value is 2.5 V. Therefore, in order to convert the single-polarity waveform to a bipolar voltage waveform whose center value is 0 V, voltage-division resistors R12 and R13 for generating a reference input of +2.5 V are provided. C4 denotes a capacitor for preventing oscillation.

Peaks of this voltage waveform (8) are held by a peak-hold circuit 33 in the following stage, whereby the voltage waveform is converted to a peak-hold waveform shown in FIG. 13 (9). As shown in FIG. 9, the DC component of the voltage waveform (8) is removed at the inlet side of the peak-hold circuit 33, by means of a high-pass filter 33a consisting of a capacitor C5 and a resistor R15. Subsequently, the voltage waveform (8) is supplied to a peak-hold section mainly consisting of an operational amplifier IC5-3 and a capacitor C6, via a current limiting resistor R26. Thus, the peak value of the voltage waveform (8) is held by means of the capacitor C6, which is connected in parallel to the output of the operational amplifier IC5-3.

The peak value of the voltage waveform (8) increases and decreases stepwise in response to changeover between the reference capacitor C3 and the sensing capacitor CS. When the peak value voltage increases, the capacitor C6 is additionally charged because of an increase in the output voltage of the operational amplifier IC5-3. Meanwhile, when the peak value voltage decreases, the potential at the capacitor C6 becomes higher than the potential at the output of the operational amplifier IC5-3. An ordinary peak-hold circuit is configured to discharge the capacitor C6 by means of current absorption into the operational amplifier IC5-3 or through self-discharge, to thereby cause the peak hold output to follow the changing peak of the voltage waveform. In contrast, in the present embodiment, the above-mentioned current absorption is prevented by means of a diode D1, and the discharge is accelerated by means of a resistor (having a high resistance of, for example, 1 MΩ) R16 disposed parallel to the capacitor C6, whereby the waveform following speed is further increased.

AS shown in FIG. 9, the thus-obtained peak-hold signal (9) (see FIG. 13 (9)) is amplified by means of an amplification section 34 in the following stage, and the thus-amplified signal is output as the final detection signal (10) (see FIG. 13 as well). In the amplification section 34, an operation amplifier IC5-4 forms a well-known non-inverted amplification circuit in cooperation with resistors R17 to R19 and a capacitor C7. Through employment of the non-inverted amplification circuit, the peak-hold signal (9) is amplified, while being subjected to impedance conversion, whereby the peak-hold signal (9) becomes unlikely to be influenced by load change of a signal processing section in the subsequent stage, noise, etc. Notably, an output protection circuit consisting of resistors R20 and R21, a capacitor C8, and a zener diode RD5 is provided to follow the non-inverted amplification circuit.

As shown in FIG. 13, the detection signal (10) has a rectangular waveform in which peak-hold values (which reflect the electrostatic capacitances of the reference capacitor C3 and the sensing capacitor CS, respectively) alternately appear in response to changeover between the reference capacitor C3 and the sensing capacitor CS. The detection signal (10) can be considered to be a type of time-division multiplexed signal obtained through time-division multiplexing of a signal representing the measured electrostatic capacitance of oil and a signal representing the measured electrostatic capacitance of the reference capacitor C3 for output compensation. In order to compensate the signal representing the measured electrostatic capacitance of oil by use of the signal representing the measured electrostatic capacitance of the reference capacitor C3, the two signals must be separated from each other in some way. In the present embodiment, as shown in FIG. 9, the frequency division circuit 3 is configured to output the changeover control signal (5) to the outside (e.g., a micro processor or analog hardware, which will be described later) via an output terminal 35. The timing in the detection signal (10) at which changeover between the reference capacitor C3 and the sensing capacitor CS is effected, and thus, timing for signal separation, can be determined on the basis of the edge timing of the changeover control signal (5).

Figure 15:
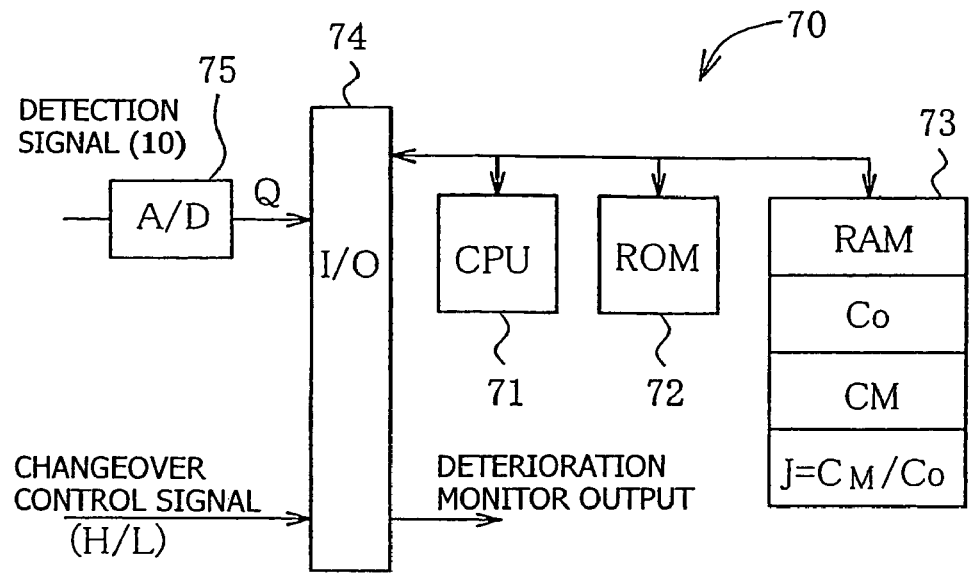
FIG. 15 is a block diagram showing an example circuit which is formed by use of a microprocessor and adapted to compensate electrostatic capacitance information of the sensing capacitor by use of output from the output compensation processing circuit of FIG. 9.

Next, an example of actual output compensation computation processing which utilizes a micro processor will be described. As shown in FIG. 15 and as is well known, the micro processor 70 includes a CPU 71, a ROM 72, which stores a control program, a RAM 73, which is used during execution of the program, and an interface section 74 for inputting and outputting signals and data. The detection signal (10) is converted to a digital signal Q having a predetermined number of bits by means of an A/D converter 75, and the digital signal Q is input to a data input port of the interface section 74. Meanwhile, the changeover control signal output from the output terminal 35 is input to another data input port of the interface section 74.

Figure 16:
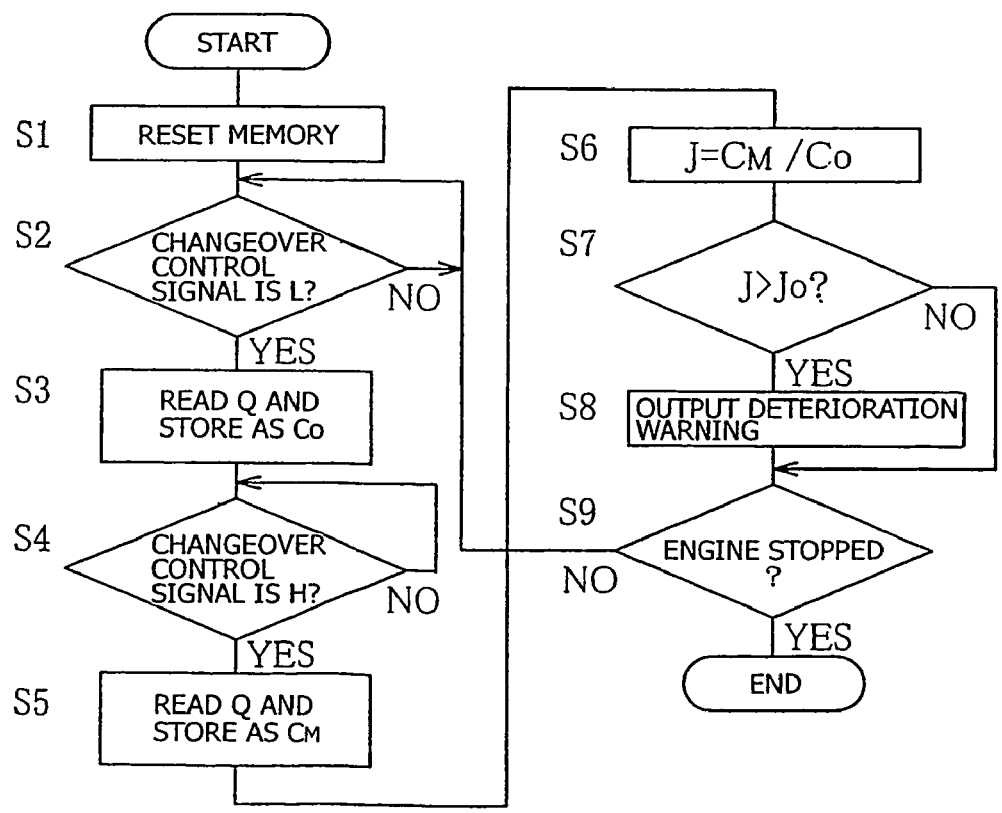
FIG. 16 is a flowchart showing the flow of a program for controlling operation of the circuit of FIG. 15.

FIG. 16 shows an example of the processing. When operation of the engine is started, and the present processing is then started, the CPU first resets a necessary memory area of the RAM 73 in step S1. Subsequently, when it is determined in step S2 that the changeover control signal output from the output terminal 35 has changed to the L level, the CPU reads the value of the digital detection signal Q. This value reflects the electrostatic capacitance of the reference capacitor C3, because the value is read when the changeover control signal is at the L level. In step S3, the CPU stores the value as Co. Subsequently, when it is determined in step S4 that the changeover control signal output from the output terminal 35 has changed to the H level, the CPU reads the value of the digital detection signal Q. This value reflects the electrostatic capacitance of the sensing capacitor CS; i.e., the electrostatic capacitance of oil whose deterioration is to be measured, because the value is read when the changeover control signal is at the H level. In step S5, the CPU stores the value as CM. In step S6, the CPU calculates a capacitance relative value J of the oil by dividing the value of CM by the value of Co. When in step S7 the value of J is determined to be greater than a limit value Jo, the CPU judges that the service life of the oil has ended. Subsequently, in step S8, the CPU performs a predetermined warning operation; e.g., turns on a lamp.

Figure 19:
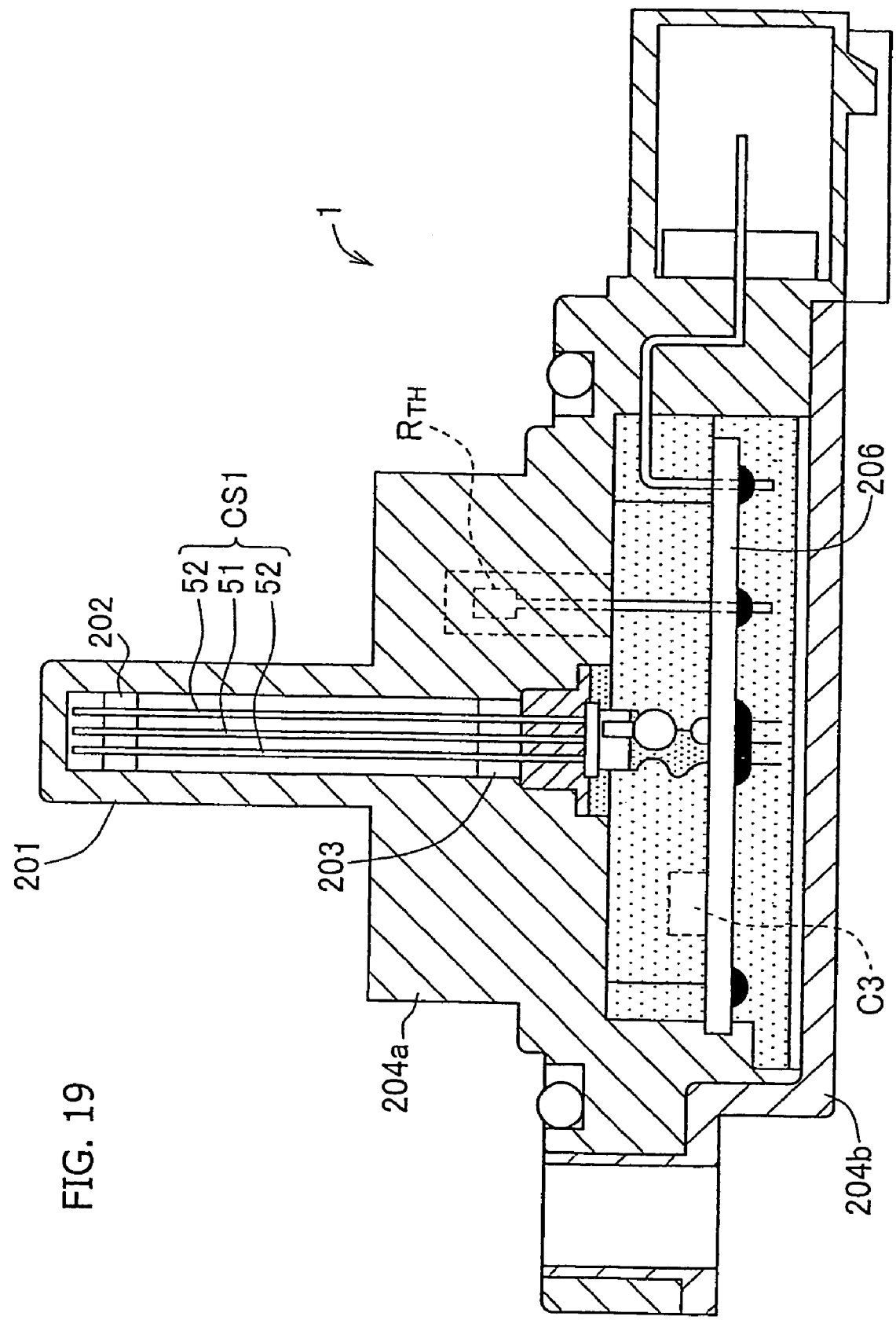
FIG. 19 is a cross sectional view showing an example structure of an engine oil deterioration detection apparatus.

FIG. 19 is a cross-sectional view showing an example structure of the oil deterioration detection apparatus 1. In this structure, in order to shorten, to the extent possible, the length of wires for connecting the sensing capacitor and peripheral circuits, a sensing capacitor CS1 and a printed circuit board 206—in which the detection signal output circuit 30 is incorporated (in the present embodiment, the measurement signal generation circuit 10, the power supply circuit 20, and the output compensation processing circuit 21 containing the reference capacitor C3 are also incorporated)—are integrally built within a case consisting of a cover unit 204a and a case body 204b. The case has an oil introduction chamber portion 201, which is sealed and isolated from the circuit board 206. The sensing capacitor CS1 is disposed within the oil introduction portion 201, into which engine oil stored in the oil pan flows through oil communication ports 202 and 203. Thus, the oil fills the gaps between the electrode plates 51 and 52 disposed within the oil introduction chamber portion 201, whereby the sensing capacitor CS1 is formed. In the present embodiment, the circuit board 206 is placed in the case body 204b, and the oil introduction chamber portion 201 is formed in the cover unit 204a, which closes the opening of the case body 204b. Further, the electrode plates 51 and 52 of the sensing capacitor CS1 project directly from the circuit board 206. Meanwhile, the reference capacitor C3 is mounted onto the circuit board 206.

Since the sensing capacitor CS1, with which hot oil comes into contact, is disposed in the vicinity of the circuit board 206 (i.e., the peripheral circuits for measurement), it is apparent that the temperature of the peripheral circuits to be used for measurement changes greatly with oil temperature, whereby the level of the detection output changes even when the degree of deterioration of the oil does not change. However, under the structure of the present invention, both the electrostatic capacitance CM of the sensing capacitor and the electrostatic capacitance Co of the reference capacitor C3 are obtained on the basis of the detection signal (10) output via the same detection signal output circuit 30. Therefore, even when the level of the detection signal changes under the influence of the temperature characteristic of the detection signal output circuit 30, CM and Co are considered to be identical in terms of influence of the level change. Therefore, the value of CM in relation to the electrostatic capacitance of the oil to be measured can be compensated through employment of the capacitance relative value J obtained by dividing the value of CM by the value of Co.

Further, stemming from long-time exposure to such high temperature, the characteristics of the peripheral circuits deteriorate to some degree, whereby the level of the detection output changes to no small extent. However, insofar as the same signal output circuit 30 is employed for CM and Co, CM and Co are considered to be identical in terms of influence of characteristic deterioration. Therefore, a similar compensation effect can be attained.

Figure 20:
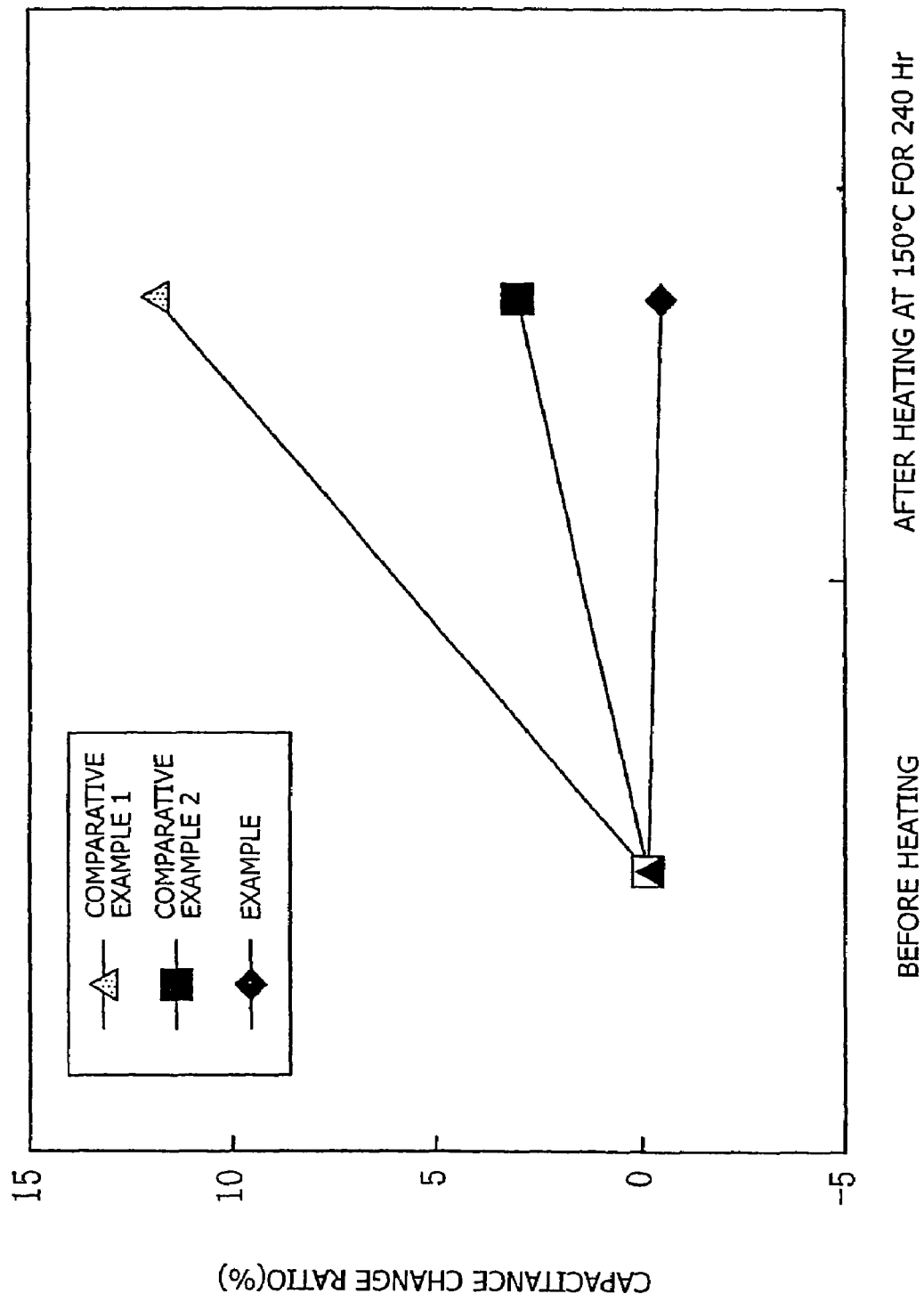
FIG. 20 is a graph showing the time-course deterioration characteristic of the reference capacitor along with those of comparative examples.

However, in this case, the compensation effect cannot be achieved if the characteristics of the reference capacitor C3 change with time. The above-described plastic film capacitor (product name: ECHU (Matsushita Electric Industrial Co., Ltd.) has a small temperature coefficient, and excellent characteristic stability under high temperature. When an accelerated test was performed while the capacitor was left in an 150° C. atmosphere for 240 hours, the change rate of the electrostatic capacitance of the capacitor was found to fall with the range of ±1%. Therefore, use of the capacitor is effective for output compensation for character deterioration of the circuit with time. FIG. 20 shows the rate of change of the electrostatic capacitance of the plastic film capacitor obtained through measurement of the electrostatic capacitance by an AC impedance method before and after the above-mentioned accelerated test, along with those of comparative examples. Comparative Example 1 shows the rate of change in the electrostatic capacitance of a sensing capacitor dipped in fresh oil (CF-4 10W-30, product of Idemitsu Kosan Co. Ltd.), which may be used as a reference capacitor for detecting deteriorated oil. Comparative Example 2 shows the rate of change in the electrostatic capacitance of a commercially available ceramic capacitor (e.g., P-GRM39B series, Murata Manufacturing Co., Ltd.). As compared with these two comparative examples, the rate of change of the electrostatic capacitance of the example capacitor is considerably low, which demonstrates that the example capacitor is suitable for the reference capacitor for compensating time-course deterioration.

Figure 17:
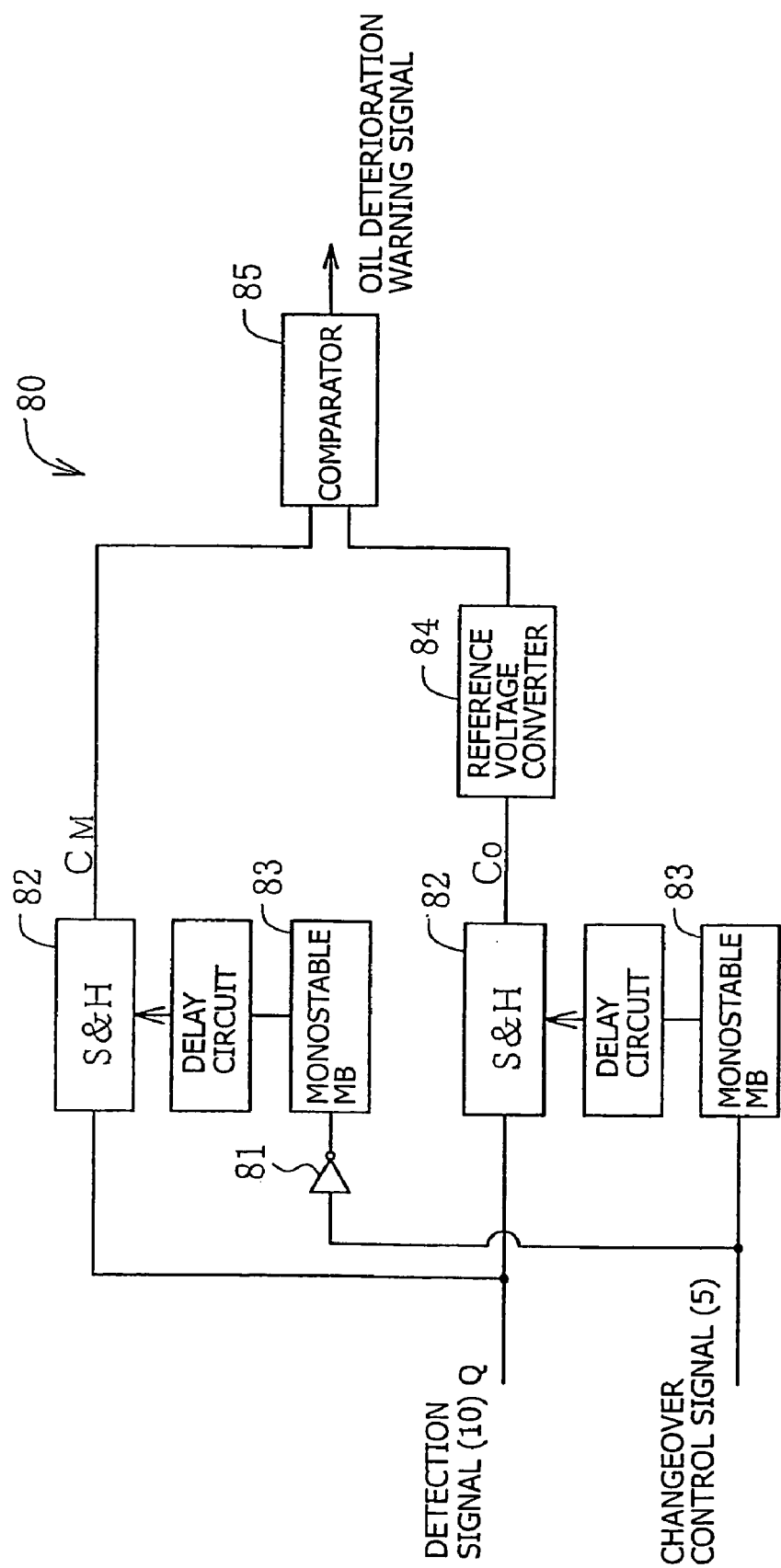
FIG. 17 is a block diagram showing an example circuit which is formed by use of analog hardware and adapted to compensate electrostatic capacitance information of the sensing capacitor by use of output from the output compensation processing circuit of FIG. 9.

Notably, the output compensation computation processing can be performed by use of analog hardware 80 as shown in FIG. 17, without use of the microprocessor. The detection signal (10) is distributed to two sample-hold circuits 82, each of which samples and holds the detection signal (10) upon receipt of a pulse from a corresponding monostable multivibrator 83. The monostable multivibrator 83 generates the pulse, while using the falling edge of each clock pulse as an activation trigger. Although the above-described changeover control signal (see FIG. 1) output from the output terminal 35 is used as the clock pulse, the changeover control signal is supplied to one of the monostable multivibrators 83 via an inverter 81. By virtue of the above-described configuration, one sample-hold circuit 82 samples the detection signal (10) at a point in time corresponding to the rising edge of the changeover control signal, whereas the other sample-hold circuit 82 samples the detection signal (10) at a point in time corresponding to the falling edge of the changeover control signal. The detection signal (10) sampled by the former sample-hold circuit 82 is output as an analog signal CM reflecting the electrostatic capacitance of the sensing capacitor CS, and the detection signal (10) sampled by the latter sample-hold circuit 82 is output as an analog signal Co reflecting the electrostatic capacitance of the reference capacitor. In consideration of the fact that the detection signal (10) becomes stable after elapse of a certain period of time from each changeover edge, a delay circuit is provided between each of the sample-hold circuits 82 and the corresponding monostable multivibrator 83.

The processing for obtaining J by dividing CM by Co may be performed by use of an analog division circuit using a logarithmic transformation circuit or the like. However, in the case where the above-mentioned limit value Jo can be set to a constant, from the relation Jo=CM/Co, the relation CM=Jo·Co can be obtained. Therefore, Co is amplified at a gain corresponding to Jo by means of a reference voltage converter 84 consisting of an non-inverted amplifier, and the output from the reference voltage converter 84 is supplied, as a reference value, to a comparator 85 for comparison with the value of CM. Thus, determination of oil deterioration can be performed.

Finally, the constant-voltage power supply circuit 20 of FIG. 1 will be described. The constant-voltage power supply circuit 20 includes a first power supply section 21 in a front stage, and a second power supply section 22 in a rear stage. The first power supply section 21 receives electricity from a battery (not shown) mounted on a vehicle. After a superposed AC component output from an alternator or the like is removed by means of a low-pass filter consisting of a resistor R23 and a capacitor C9, the electricity flows into a bypass circuit including a current limiting resistor R24 and a zener diode ZD2, whereby the zener diode ZD2 produces a constant voltage. This constant voltage is applied to a transistor Tr1 so as to drive the same. As a result, a constant DC voltage can be output from the input electricity. Notably, C10 denotes a capacitor for oscillation prevention, and D1 denotes a diode for preventing reverse flow. In the present embodiment, the output voltage of the first power supply section 21 is +7.6 V, and is used as the power supply voltage for the operational amplifiers IC5-1 to IC5-4, etc.

The second power supply section 22 includes a three-terminal regulator IC7, and generates a more stable DC voltage which is less affected by temperature change and other factors. The output from the first power supply section 21 is supplied to the three-terminal regulator IC7. The three-terminal regulator IC7 slightly steps down the supplied voltage to +5 V, which is supplied to the already-described various integrated circuits IC1 to IC4 and IC6 as drive voltage, and is further supplied to the set voltage generation section 10 as base voltage for generation of set voltages. While using the second power supply section 22 as a single power supply section, the set voltage generation section 10 generates various analog set voltages by means of voltage division circuits. Notably, C12 denotes a capacitor for oscillation prevention, and bypass capacitors C13 to C17 are connected parallel to the integrated circuits IC1 to IC4 and IC6.

Although the embodiment of the present invention has been described, the present invention is not limited thereto. The embodiment may be modified or improved in various ways without departing from the scope of the invention described in the appended claims, and modified or improved embodiments fall within the technical scope of the present invention. For example, the embodiment may be modified to measure the temperature of oil under measurement by use of a temperature sensor such as a thermistor, so as to compensate for influence of temperature change of the oil under measurement, as well as influence of temperature change of the detection signal output circuit 30. By virtue of this configuration, the detection of oil deterioration on the basis of change in electrostatic capacitance can be performed more accurately. Specifically, the relation between electrostatic capacitance correction coefficient and oil temperature is measured in advance by, for example, an experiment; and the relation is stored, as electrostatic-capacitance-correction-coefficient vs. oil-temperature relation information, in the ROM 72 of FIG. 15 or the like, in the form of a single-dimension map or an empirical formula. Further, a step for measuring oil temperature is added between steps S1 and S2 of the flowchart shown in FIG. 7, and a step for determining an electrostatic capacitance correction coefficient for the measured oil temperature, with reference to the electrostatic-capacitance-correction-coefficient vs. oil-temperature relation information and through interpolation or calculation by use of an empirical formula is added between steps S6 and S7. The relative capacitance value J calculated in step S6 is multiplied by the electrostatic capacitance correction coefficient so as to obtain a corrected relative capacitance value J'. In step S7, the determination regarding oil deterioration (service life) is performed on the basis of the results of comparison between the corrected relative capacitance value J' and the limit value Jo.

In the above-described embodiment, a capacitance relative value is calculated in order to compensate the electrostatic capacitance of the sensing capacitor for the influence of the temperature characteristic of the circuit. However, when the circuit temperature is fixed to a constant temperature, the influence of temperature change on the measured value can be avoided. In this case, a physical quantity (e.g., oil temperature) reflecting the circuit temperature is monitored by use of a temperature detection element, and when the circuit temperature reaches a prescribed value, deterioration detection is performed. A thermistor $R_{TH}$ as shown in FIG. 19 can be used as the temperature detection element. For example, as shown in FIG. 9, a change in the resistance of the thermistor $R_{TH}$ is reflected in a divided voltage generated through voltage division by the thermistor $R_{TH}$ and a fixed resistor R30, and the divided voltage is distributed to comparators 41 and 42 as a measurement voltage Vs. Further, a gate 43 is provided in order to obtain the logical product of outputs of the two comparators 41 and 42. In this circuit, only when the measurement voltage Vs falls between reference voltages Vref1 and Vref2 (i.e., only when the temperature measured by the thermistor $R_{TH}$ falls within a predetermined range), the output of the gate 43 is activated by the outputs of the comparators 41 and 42. A switch 40 for passing or blocking the detection output (10) is provided, and is driven by the output of the gate 43. This configuration enables the detection output (10) to be output only when the circuit temperature falls within a predetermined range. Even in this configuration, the influence of time-course deterioration of the circuit can be compensated for by use of a reference capacitor. Notably, in the apparatus structure of FIG. 19, the thermistor $R_{TH}$ is embedded in the cover unit 204a, which comes into contact with oil within the oil pan.

The invention claimed is:

1. An oil deterioration detection apparatus comprising a sensing capacitor formed of paired electrodes dipped into oil whose deterioration is to be detected, the oil deterioration detection apparatus detecting deterioration of the oil on the basis of a change in electrostatic capacitance of the sensing capacitor, the apparatus comprising:
   a measurement signal generation circuit for generating a measurement signal to be supplied to the sensing capacitor in order to measure the electrostatic capacitance of the sensing capacitor;
   a detection signal output circuit for outputting a detection signal on the basis of a response wave signal produced from the sensing capacitor in response to supply of the measurement signal thereto, the detection signal reflecting the electrostatic capacitance of the sensing capacitor; and
   an output compensation mechanism for compensating the detection signal for an output level change stemming from a temperature characteristic and/or a time-course deterioration of the detection signal output circuit;
   wherein the output compensation mechanism comprises a reference element whose impedance temperature coefficient is smaller than that of the sensing capacitor; and an output compensation processing circuit for performing output compensation for the detection signal on the basis of a measured impedance of the reference element;
   wherein the reference element is a reference capacitor; and the output compensation processing circuit measures electrostatic capacitance of the reference capacitor through measurement of impedance of the reference capacitor; and
   wherein the reference capacitor has an electrostatic capacitance temperature coefficient of +1% or less within a temperature range of −30° C. to 120° C., wherein an electrostatic capacitance at 20° C. is used as a reference.

2. An oil deterioration detection apparatus according to claim 1, wherein the output compensation processing circuit comprises a measurement signal generation circuit for generating a measurement signal to be supplied to the reference element, and a detection signal output circuit for outputting a detection signal on the basis of a response wave signal produced from the reference element in response to supply of the measurement signal thereto, the detection signal reflecting the impedance of the reference element; and the output compensation is performed on the basis of the result of comparison between sensor impedance measurement information based on the detection signal reflecting the impedance of the sensing capacitor and reference element impedance measurement information reflecting the impedance of the reference element.

3. An oil deterioration detection apparatus according to claim 1, wherein the measurement signal generation circuit and the detection signal output circuit of the output compensation processing circuit are shared between the sensing capacitor and the reference element; and a changeover circuit is provided in order to selectively connect these circuits to the sensing capacitor or the reference element.

4. An oil deterioration detection apparatus according to claim 3, further comprising a changeover control mechanism for causing the changeover circuit to repeatedly perform the changeover of the circuit connection at constant intervals.

5. An oil deterioration detection apparatus according to claim 1, wherein the electrostatic capacitance of the reference capacitor changes ±1% or less after the capacitor is left for 240 hours at 150° C.

6. An oil deterioration detection apparatus according to claim 1, wherein the measurement signal generation circuit generates a sinusoidal signal as the measurement signal; and the detection signal output circuit outputs, as the detection signal, the peak value of the waveform of a response wave signal generated as a result of application of the sinusoidal signal and amplified at a predetermined amplification factor.

7. An oil deterioration detection apparatus according to claim 1, wherein the measurement signal generation circuit comprises:
a voltage output section for selecting and outputting one of a plurality of analog set voltages; and
a voltage output control section for controlling the voltage output of the voltage output section in such a manner that the plurality of analog set voltages are selected in a predetermined sequence and at predetermined intervals in order to produce a stepped voltage output.

8. An oil deterioration detection apparatus according to claim 7, wherein the measurement signal generation circuit comprises:
an analog switch circuit having a plurality of voltage input ports supplied with respective constant analog set voltages, a voltage output port for selectively outputting one of the plurality of analog set voltages supplied to the voltage input ports, and a changeover circuit for selecting an analog set voltage to be output to the voltage output port on the basis of a changeover selection signal supplied from the outside; and
a changeover selection signal output circuit for outputting the changeover selection signal to the analog switch circuit such that the plurality of analog set voltages are selectively output from the analog switch circuit in a predetermined sequence,
wherein a stepped waveform produced by selective output of the analog set voltages in accordance with the output sequence of the changeover selection signal is output, as a signal waveform, from the voltage output port of the analog switch circuit.

9. An oil deterioration detection apparatus according to claim 8, wherein
the measurement signal generation circuit includes an oscillation circuit whose oscillation section is formed by use of a ceramic oscillator or a quartz oscillator; and the changeover selection signal output circuit selectively outputs the plurality of analog set voltage s at changeover timings of constant intervals, which are determined on the basis of the oscillation frequency of the oscillation circuit, in order to obtain a signal waveform which includes a repeated, stepped signal waveform unit formed through output of three or more analog set voltages in a fixed sequence.

10. An oil deterioration detection apparatus comprising a sensing capacitor formed of paired electrodes dipped into oil whose deterioration is to be detected, the oil deterioration detection apparatus detecting deterioration of the oil on the basis of a change in electrostatic capacitance of the sensing capacitor, the apparatus comprising:
a measurement signal generation circuit for generating a measurement signal to be supplied to the sensing capacitor in order to measure the electrostatic capacitance of the sensing capacitor;
a detection signal output circuit for outputting a detection signal on the basis of a response wave signal produced from the sensing capacitor in response to supply of the measurement signal thereto, the detection signal reflecting the electrostatic capacitance of the sensing capacitor; and
an output compensation mechanism for compensating the detection signal for an output level change stemming from a temperature characteristic and/or a time-course deterioration of the detection signal output circuit,
wherein the measurement signal generation circuit comprises:
a voltage output section for selecting and outputting one of a plurality of analog set voltages; and
a voltage output control section for controlling the voltage output of the voltage output section in such a manner that the plurality of analog set voltages are selected in a predetermined sequence and at predetermined intervals in order to produce a stepped voltage output.

11. An oil deterioration detection apparatus according to claim 10, wherein the output compensation mechanism comprises a reference element whose impedance temperature coefficient is smaller than that of the sensing capacitor; and an output compensation processing circuit for performing output compensation for the detection signal on the basis of a measured impedance of the reference element.

12. An oil deterioration detection apparatus according to claim 11, wherein the output compensation processing circuit comprises a measurement signal generation circuit for generating a measurement signal to be supplied to the reference element, and a detection signal output circuit for outputting a detection signal on the basis of a response wave signal produced from the reference element in response to supply of the measurement signal thereto, the detection signal reflecting the impedance of the reference element; and
the output compensation is performed on the basis of the result of comparison between sensor impedance measurement information based on the detection signal reflecting the impedance of the sensing capacitor and reference element impedance measurement information reflecting the impedance of the reference element.

13. An oil deterioration detection apparatus according to claim 12, wherein the measurement signal generation circuit and the detection signal output circuit of the output compensation processing circuit are shared between the sensing capacitor and the reference element; and a changeover circuit is provided in order to selectively connect these circuits to the sensing capacitor or the reference element.

14. An oil deterioration detection apparatus according to claim 13, further comprising a changeover control mechanism for causing the changeover circuit to repeatedly perform the changeover of the circuit connection at constant intervals.

15. An oil deterioration detection apparatus comprising:
a sensing capacitor formed of paired electrodes to be dipped into oil; and
a reference element having a smaller impedance temperature coefficient than that of said sensing capacitor, wherein said oil deterioration detection apparatus detects deterioration of the oil on the basis of comparison between a corrected relative capacitance value and a relative limit value thereof; and
wherein said corrected relative capacitance value is obtained by multiplying a relative capacitance value with an electrostatic capacitance correction coefficient, and wherein said relative capacitance value is a ratio of sensor impedance measurement information reflecting the impedance of the sensing capacitor to reference element impedance measurement information reflecting the impedance of said reference element.

* * * * *